US006814071B2

(12) United States Patent
Klimowicz et al.

(10) Patent No.: US 6,814,071 B2
(45) Date of Patent: *Nov. 9, 2004

(54) METHODS AND APPARATUS FOR AEROSOLIZING A SUBSTANCE

(75) Inventors: Mike Klimowicz, Los Altos, CA (US); Yehuda Ivri, Irvine, CA (US)

(73) Assignee: Aerogen, Inc., Sunnyvale, CA (US)

( * ) Notice: Subject to any disclaimer, the term of this patent is extended or adjusted under 35 U.S.C. 154(b) by 68 days.

This patent is subject to a terminal disclaimer.

(21) Appl. No.: 10/201,341

(22) Filed: Jul. 22, 2002

(65) Prior Publication Data

US 2002/0185125 A1 Dec. 12, 2002

Related U.S. Application Data

(63) Continuation of application No. 09/483,096, filed on Jan. 14, 2000, now Pat. No. 6,427,682, which is a continuation-in-part of application No. 09/313,914, filed on May 18, 1999, which is a continuation-in-part of application No. 09/149,426, filed on Sep. 8, 1998, now Pat. No. 6,205,999, which is a continuation-in-part of application No. 09/095,737, filed on Jun. 11, 1998, now Pat. No. 6,014,970, which is a continuation of application No. 08/417,311, filed on Apr. 5, 1995, now Pat. No. 5,938,117.

(51) Int. Cl.$^7$ .............................................. B05B 17/06
(52) U.S. Cl. ............................ 128/200.16; 128/200.14; 239/338
(58) Field of Search ..................... 128/200.14–200.24; 604/58–60, 68–72, 518, 82–92, 19, 22, 131–155; D24/110; 239/337–373, 142, 327, 328; 141/325

(56) References Cited

U.S. PATENT DOCUMENTS

| | | | | |
|---|---|---|---|---|
| 4,465,234 A | * | 8/1984 | Maehara et al. | 239/102.2 |
| 4,613,326 A | * | 9/1986 | Szwarc | 604/89 |
| 5,435,282 A | * | 7/1995 | Haber et al. | 128/200.16 |
| 6,014,970 A | * | 1/2000 | Ivri et al. | 128/200.16 |
| 6,205,999 B1 | * | 3/2001 | Ivri et al. | 128/200.22 |
| 6,427,682 B1 | * | 8/2002 | Klimowicz et al. | 128/200.16 |

* cited by examiner

Primary Examiner—Glenn K. Dawson
(74) Attorney, Agent, or Firm—Townsend and Townsend and Crew LLP

(57) ABSTRACT

A device for aerosolizing a liquid includes a chamber having a deformable wall which expands and contracts as fluid is delivered and expelled from a fluid chamber. The chamber is partially bounded by a vibrating structure having holes therein for expelling the fluid. In another aspect, the invention provides exemplary aerosolization apparatus and methods for aerosolizing a substance. A liquid is transferred from a first chamber into a second chamber having a substance that is in a dry state to form a solution. The solution is then transferred from the second chamber and onto an atomization member. The atomization member is operated to aerosolize the solution.

12 Claims, 26 Drawing Sheets

METHODS AND APPARATUS FOR AEROSOLIZING A SUBSTANCE

CROSS-REFERENCES TO RELATED APPLICATIONS

This application is a continuation of U.S. patent application Ser. No. 09/483,096, filed Jan. 14, 2000, now U.S. Pat. No. 6,427,682, which is a continuation in part application of U.S. patent application Ser. No. 09/313,914, filed May 18, 1999, now pending which is a continuation in part of Ser. No. 09/149,426, filed Sep. 8, 1998 now U.S. Pat. No. 6,205,999, which is a continuation in part of Ser. No. 09/095,737, filed Jun. 11, 1998 now U.S. Pat. No. 6,014,970, which is a continuation in part of Ser. No. 08/417,311, filed Apr. 5, 1995 now U.S. Pat. No. 5,938,117, the complete disclosures of which are herein incorporated by reference.

BACKGROUND OF THE INVENTION

The invention relates generally to the field of inhalation drug therapy, and in particular to the inhalation of aerosolized chemical substances. In one aspect, the invention provides a portable inhaler having a cartridge for storing a chemical substance in a dry state and a liquid dispenser to introduce a liquid to the substance to form a solution. Immediately after formation of the solution, the inhaler aerosolizes the solution so that it may be administered to a patient.

The atomization of liquid medicaments is becoming a promising way to effectively deliver many medicaments to a patient. In particular there is a potential for pulmonary delivery of protein peptides and other biological entities. Many of these are easily degraded and become inactive if kept in a liquid form. Proteins and peptides often exhibit greater stability in the solid state. This results primarily from two factors. First, the concentration of water, a reactant in several protein degradation pathways, is reduced. See Stability of Protein Phannaceuticals, M. C. Manning, K. Patel, and R. T. Borchardt, Pharm. Res. 6, 903–918 (1989), the complete disclosure of which is herein incorporated by reference. Second, the proteins and other excipients are immobilized in the solid state. Water is a reactant in hydrolysis reactions, including peptide change and cleavage, and deamidation. Reducing the water concentration by freeze-drying or spray drying, reduces this reactant concentration and therefore the rates of these degradation pathways.

The mobility of the peptides or proteins, as well as other molecules in the formulation, are reduced in the solid or dry state. See Molecular Mobility of Amorphous Pharmaceutical Solids Below Their Glass Transition Temperatures, B. C. Hancock, S. L. Shamblin, and G. Zografi, Pharm. Res. 12, 799–806 (1995), the complete disclosure of which is herein incorporated by reference. For the peptides or proteins, this reduces the rate of intermolecular interactions as well as intramolecular conformational changes or fluctuations in conformation. Minimization of intermolecular interactions will reduce protein and peptide aggregation/precipitation, and will also reduce the rate of diffusion of chemical reactants to the protein or peptide which will slow the rate of chemical degradation pathways. Reduction in intramolecular conformational changes reduces the rate at which potentially reactive groups become available for chemical or intermolecular interaction. The rate of this reaction may decrease as the water concentration, and mobility of the protein, is reduced.

One way to produce protein in solid or dry state is to transform the liquid into a fine powder. When used for inhalation delivery, such powders should be composed of small particles with a mean mass diameter of 1 to 5 microns, with a tight particle size distribution. However, this requirement increases the processing and packaging cost of the dry powder. See also U.S. Pat. No. 5,654,007 entitled "Methods and System for Processing Dispersible Fine Powders" and U.S. Pat. No. 5,458,135 entitled "Methods and Devices for Delivering Aerosolized Medicaments", the disclosures of which are incorporated herein by reference.

An easier way to transform a liquid solution to solid or dry form is to use a freeze drying process where a liquid solution is converted to a solid substance that can be readily reconstituted to a liquid solution by dissolving it with a liquid, such as water. Hence, one object of the present invention is to provide a way to store a solid substance and combine the solid substance the with a liquid to form a solution. Once the solution is formed, it is another object of the invention to rapidly transport the solution to an atomization device to allow the solution to be aerosolized for administration. In this way, the solution is aerosolized immediately after its reconstitution so that the degradation rate of the substance is reduced.

A variety of nebulization devices are available for atomizing liquid solutions. For example, one exemplary atomization apparatus is described in U.S. Pat. No. 5,164,740, issued to Ivri ("the '740 patent"), the complete disclosure of which is herein incorporated by reference. The '740 patent describes an apparatus which comprises an ultrasonic transducer and an aperture plate attached to the transducer. The aperture plate includes tapered apertures which are employed to produce small liquid droplets. The transducer vibrates the plate at relatively high frequencies so that when the liquid is placed in contact with the rear surface of the aperture plate and the plate is vibrated, liquid droplets will be ejected through the apertures. The apparatus described in the '740 patent has been instrumental in producing small liquid droplets without the need for placing a fluidic chamber in contact with the aperture plate, as in previously proposed designs. Instead, small volumes of liquid can be placed on the rear surface of the aperture plate and held to the rear surface by surface tension forces.

A modification of the '740 apparatus is described in U.S. Pat. Nos. 5,586,550 ("the '550 patent") and 5,758,637 ("the '637 patent"), the complete disclosures of which are herein incorporated by reference. These two references describe a liquid droplet generator which is particularly useful in producing a high flow of droplets in a narrow size distribution. As described in the '550 patent, the use of a non-planar aperture plate is advantageous in allowing more of the apertures to eject liquid droplets. Furthermore, the liquid droplets may be formed within the range from about 1 $\mu$m to about 5 $\mu$m so that the apparatus will be useful for delivering drugs to the lungs.

Hence, it is a further objective of the invention to provide devices and methods to facilitate the transfer of liquid solutions (preferably those which have just been reconstituted) to such aerosolizing apparatus so that the solution may be atomized for inhalation. In so doing, one important consideration that should be addressed is the delivery of the proper dosage. Hence, it is still another object of the invention to ensure that the proper amount of liquid medicament is transferred to an aerosol generator so that a proper dosage may be delivered to the lungs.

In still another aspect of the present invention, the present invention is directed to methods and devices for delivering fluids to a vibrating element

SUMMARY OF THE INVENTION

The invention provides exemplary systems, apparatus and methods for reconstituting a solid phase substance, e.g., a substance that is in a dry state, with liquid to form a solution and for transporting the solution to an aerosol generator for subsequent atomization. In one exemplary embodiment, the system comprises a liquid dispenser, a cartridge containing a substance in a dry state, and an aerosol generator. In use, the cartridge is coupled to an outlet of the dispenser and the dispenser is operated to dispense liquid from the outlet and into the cartridge. The liquid then flows through the substance and exits the cartridge as a solution.

In an exemplary aspect, the cartridge is replaced and disposed after each use. After removal of the cartridge the user may optionally operate the liquid dispenser to deliver liquid to the aerosol generator for a subsequent cleaning cycle. In another exemplary aspect, a liquid outlet of the cartridge is positioned near the aerosol generator such that the solution is dispensed onto the aerosol generator and is readily available for atomization.

The Liquid Dispenser

In an exemplary embodiment, the liquid dispenser comprises a mechanical pump that is attached to a canister. The liquid dispenser is disposed within a housing of the inhaler and is configured to deliver a predetermined volume of liquid each time the mechanical pump is operated. The dispensed liquid then flows directly from the pump to the cartridge to form a solution which in turn is deposited on the aerosol generator.

In one particular aspect, the liquid is a saline solution or sterile water and may optionally contain an anti-microbial additive. As previously mentioned, the solid substance in the cartridge preferably comprises a chemical that is in the dry state which is reconstituted into a solution upon introduction of the liquid from the liquid dispenser.

In one particularly preferable aspect, the mechanical pump comprises a piston pump that is connected to the canister. The piston pump comprises a spring-loaded piston member that is slidable within a cylindrical member which defines a metering chamber. When the piston member is moved to a filling position, the metering chamber is filled with liquid from the canister. When released, the piston member moves to a dispensing position to dispense a known volume of liquid from the metering chamber. In this way, each time the pump is operated, a unit volume of liquid is dispensed from the piston pump.

In one particularly preferable aspect, movement of the piston member toward the filling position creates a vacuum inside the cylindrical member that gradually increases until the piston member reaches a point where a passage is provided between the piston member and the cylindrical member. At this point, the piston member has reached the filling position to allow liquid from the canister to be drawn by the vacuum into the metering chamber of the cylinder. At this point, the piston member is released and returns by the force of the spring back to the dispensing position. During the return travel of the piston member to the dispensing position, the liquid in the metering chamber is displaced through an outlet of the pump.

In another particular aspect, the piston pump is configured to deliver volumes of liquid in the range of about 10 $\mu$L to about 50 $\mu$L each time the pump is operated. In another aspect, the piston pump is configured such that it will dispense a full unit volume only if the user fully depresses the piston to the filling position. If the piston member is only partially depressed, no liquid will be dispensed. In this manner, partial dosing is prevented.

In still yet another aspect, the liquid dispenser further includes a valve which serves to eliminate the dead volume in the piston pump, thereby inhibiting microbial inflow into the liquid dispenser. The valve preferably comprises a tubular valve seat that is slidably disposed about a distal end of the piston member. In this way, the liquid within the metering chamber moves the tubular valve seat distally over the piston member to allow the liquid in the metering chamber to be dispensed by flowing between the piston member and the tubular valve seat when the piston member is moved toward the dispensing position. The tubular valve seat is also slidable within the cylindrical member, and the cylindrical member defines a stop to stop distal movement of the tubular valve seat relative to the piston member after the unit volume of liquid has been dispensed from the metering chamber. Further, when the spring forces the distal end of the piston member into a distal end of the tubular valve seat, a seal is provided between the piston member and the tubular valve seat to prevent microbial inflow into the piston pump. Hence, use of the tubular valve seat in combination with the piston member and the cylindrical member allows for a unit volume of the liquid within the piston pump to be dispensed and further provides a seal to prevent microbial inflow into the piston pump.

The Drug Cartridge

The cartridge of the invention allows for the storage of a chemical in a dry state. When a liquid is introduced into the cartridge, the chemical substance dissolves within the liquid to form a solution just prior to aerosolization of the solution.

In one exemplary embodiment, the cartridge comprises a housing having an inlet opening and an outlet opening. Disposed in the housing is a chemical substance which is in a dry state. As liquid flows through the housing, the substance dissolves and flows through the outlet opening as a solution. The chemical substance may be any one of a variety of chemical substances, such as proteins, peptides, small molecule chemical entities, genetic materials, and other macromolecules and small molecules used as pharmaceuticals. One particular substance is a lyophilized protein, such as interferon alpha or alpha 1 prolastin. The lyophilized substance is preferably held in a support structure to increase the surface area that is in contact with the liquid, thereby increasing the rate by which the substance is dissolved. The support structure is preferably configured to hold the lyophilized substance in a three-dimensional matrix so that the surface area of the substance that is contact with the liquid is increased. Exemplary types of support structures include open cell porous materials having many tortuous flow paths which enhance mixing so that the solution exiting from the outlet end is homogenized. Alternatively, the support structure may be constructed of a woven synthetic material, a metal screen, a stack of solid glass or plastic beads, and the like.

When used in connection with the aerosolizing apparatus of the invention, actuation of the liquid dispenser introduces liquid into the inlet opening, through the support structure to dissolve the substance, and out the outlet opening where it is disposed on the aerosol generator as a solution. The aerosol generator is then operated to aerosolize the solution. In this way, the substance is stored in a solid state until ready for use. As previously described, the flow of liquid from the liquid dispenser is produced during the return stroke of the piston member, i.e. as the piston member travels to the dispensing position. Since the return stroke is controlled by the spring, it is not dependent on the user. In this way, the flow rate is the same each time the liquid dispenser is operated, thereby providing a way to consistently and repeatedly reconstitute the solution.

In one particular aspect, the cartridge includes a coupling mechanism at the inlet opening to couple the cartridge to the liquid dispenser. In this way, the cartridge is configured to be removable from the liquid dispenser so that it may be removed following each use and discarded. In still another aspect, the cartridge is filled with the chemical substance while in a liquid state. The substance is then freeze dried and converted to a solid state while in the cartridge.

The Aerosol Generator

In an exemplary embodiment, the aerosol generator that is employed to aerosolize the solution from the cartridge is constructed in a manner similar to that described in U.S. Pat. Nos. 5,586,550 and 5,758,637, previously incorporated herein by reference. In brief, the aerosol generator comprises a vibratable member having a front surface, a rear surface, and a plurality of apertures which extend between the two surfaces. The apertures are preferably tapered as described in U.S. Pat. No. 5,164,740, previously incorporated herein by reference. In one particular aspect, the vibratable member is preferably hemispherical in shape, with the tapered apertures extending from the concave surface to the convex surface. In use, the solution from the cartridge is supplied to the rear surface of the vibratable member having the large opening. As the vibratable member is vibrated, the apertures emit the solution from the small openings on the front surface as an aerosolized spray. The user then simply inhales the aerosolized spray to supply the chemical to the patient's lungs.

Alternative Embodiments

The invention further provides exemplary methods and apparatus for aerosolizing a solution. In one exemplary embodiment, an apparatus comprises a cartridge having a first chamber, a second chamber, and a moveable divider between the first and the second chambers. An exit opening is included in the cartridge and is in communication with the second chamber. A liquid is disposed in the first chamber, and a substance that is in a dry state is in the second chamber. The apparatus further includes a piston that is translatable within the cartridge to transfer the liquid from the first chamber and into the second chamber to form a solution. An aerosol generator is further provided and is disposed near the exit opening to receive the solution from the cartridge and produce an aerosolized solution. In this way, the substance may be maintained in a dry state as with other embodiments until ready for aerosolization. To form the solution, the piston is moved within the cartridge to force the liquid from the first chamber and into the second chamber. Further translation of the piston forces the recently formed solution from the second chamber and onto the aerosol generator where the solution is aerosolized.

In one particular aspect, the divider has a home position where a seal is formed between the divider and the cartridge. In this way, the liquid may be held in the first chamber until the piston is translated. Preferably, the cartridge includes at least one groove that is disposed at least part way between the first and second chambers. In this way, as the piston is moved within the first chamber, the liquid (which is generally incompressible) moves the divider toward the second chamber to allow the liquid to pass around the divider and into the second chamber. The groove preferably terminates at the second chamber so that when the piston moves the divider into the second chamber, a seal is formed between the cartridge and the divider to force the solution from the second chamber and out the exit opening.

In some cases, it may be desirable to draw the solution back into the first chamber to facilitate mixing. This can be accomplished by withdrawing the piston back through the first chamber to create a vacuum in the first chamber. To dispense the solution, the piston is translated back through the first and second chambers as previously described.

In one particular aspect, a filter is disposed across the exit opening to prevent larger particles from exiting the chamber and clogging the aerosol generator. In another aspect, the apparatus includes a motor to translate the piston. In this way, an aerosolized solution may be supplied to the patient simply by actuating the motor.

In yet another aspect of the present invention, the present invention is also directed to a device for aerosolizing a liquid having a chamber with a deformable wall. The wall moves between collapsed and expanded positions to accommodate varying volumes of fluid. The chamber moves to the expanded position in response to fluid being delivered to the chamber and collapses as fluid is expelled. The chamber contains a volume of 10–1000 $\mu$L, more preferably 10–750 $\mu$L, and most preferably 10–500 $\mu$L, while preferably maintaining the fluid pressure of less than 15 psi in the chamber. A container, which holds enough liquid to fill the chamber at least three times, delivers fluid to the chamber. The wall may be attached to the vibrating structure or may be replaced with the container.

The device preferably has a valve positioned between the container and the chamber to isolate the chamber from the container. The valve may be formed with the wall so that the valve forms part of the wall. The valve is preferably positioned less than 1 mm from the back side of the vibrating structure so that the chamber has a low volume when collapsed. The chamber preferably has a volume of less than 5 $\mu$L and more preferably less than 2 $\mu$L when collapsed. The valve is preferably positioned adjacent to the holes in the vibrating structure.

These and other aspects and advantages of the invention are described in the following description, claims and drawings.

BRIEF DESCRIPTION OF THE DRAWINGS

FIG. 1 illustrates a partial cutaway view of an exemplary apparatus having an aerosol generator for aerosolizing liquids according to the invention.

FIG. 2 is a schematic diagram of an inhalation flow sensor for detecting when a patient begins to inhale from an aerosolizing apparatus according to the invention.

FIG. 3 is a cross-sectional side view of an aerosol generator of the aerosolizing apparatus of FIG. 1.

FIGS. 4–9 illustrate cross-sectional side views of a container and a piston pump used in the apparatus of FIG. 1 to deliver a predetermined volume of liquid to the aerosol generator. The views illustrated in FIGS. 4–9 show various states of the piston pump when metering and transferring liquids from the container to the aerosol generator.

FIG. 10 is a schematic view of an aerosolizing system having a removable cartridge holding a substance that is in a solid state according to the invention.

FIG. 11 illustrates the aerosolizing system of FIG. 10 having the cartridge removed for cleaning of the aerosol generator according to the invention.

FIG. 12 is a cross sectional side view of an alternative apparatus for aerosolizing a solution according to the invention.

FIG. 13 illustrates a dual chamber drug cartridge and an aerosol generator of the apparatus of FIG. 12.

FIGS. 14–17 illustrate the drug cartridge of FIG. 13 in various states of operation to dispense a solution onto the aerosol generator according to the invention.

FIG. 18 illustrates the apparatus of FIG. 1 with an alternative cartridge to deliver liquids to the aerosol generator according to the invention.

DESCRIPTION OF THE SPECIFIC EMBODIMENTS

The invention provides exemplary systems, apparatus and methods for reconstituting a solid substance that is in a dry state with liquid, such as water, to form a solution and for transporting the solution to an aerosol generator for subsequent atomization. In one exemplary embodiment, the system comprises a liquid dispenser, a cartridge containing the substance that is in the dry state, and an aerosol generator. In use, the cartridge is coupled to an outlet of the dispenser. The user then actuates the liquid dispenser so that liquid is dispensed from the dispenser and enters into the cartridge. As the liquid flows through the cartridge, the dry substance is dissolved into the liquid and exits the cartridge as a solution. Preferably, the cartridge is replaced and disposed after each use. In a preferred embodiment, an outlet end of the cartridge is positioned near the aerosol generator so that the solution disposed on the aerosol generator is readily available for atomization.

In one alternative, a two step process is employed to reconstitute the solution and deliver the solution to the aerosol generator. First, a portion of a unit volume of liquid, such as one-half a unit volume, is supplied to the cartridge when the liquid dispenser is operated. The user then waits a predetermined amount of time, such as about 10 seconds, and again operates the liquid dispenser to deliver sufficient liquid into the cartridge to force a unit volume of solution from the cartridge an onto the aerosol generator. In this way, a period of time is provided to allow more of the substance to dissolve in the liquid.

In another aspect of the invention, exemplary systems and methods are provided for metering relatively small volumes of liquid directly from a container and for delivering the metered volume to an atomizer. The systems and methods are configured to precisely meter and deliver relatively small volumes of liquid, typically in the range from about 10 $\mu$L to about 100 $\mu$L. When delivering volumes in the range from about 10 $\mu$L to 50 $\mu$L, the invention preferably employs the use of a piston pump that is connected to a canister as described in greater detail hereinafter. For volumes in the range from about 50 $\mu$L to about 100 $\mu$L, a pharmaceutical pump is preferably employed, such as metered dose S4 pump, commercially available from Somova S. p.A. Milano, Italy. Optionally, such pharmaceutical pumps may also contain a pharmaceutical medicament which may be delivered directly to the aerosol generator. As one example, the pharmaceutical medicament may comprise a suspension of colica steroid for treatment of asthma.

Figure 1:
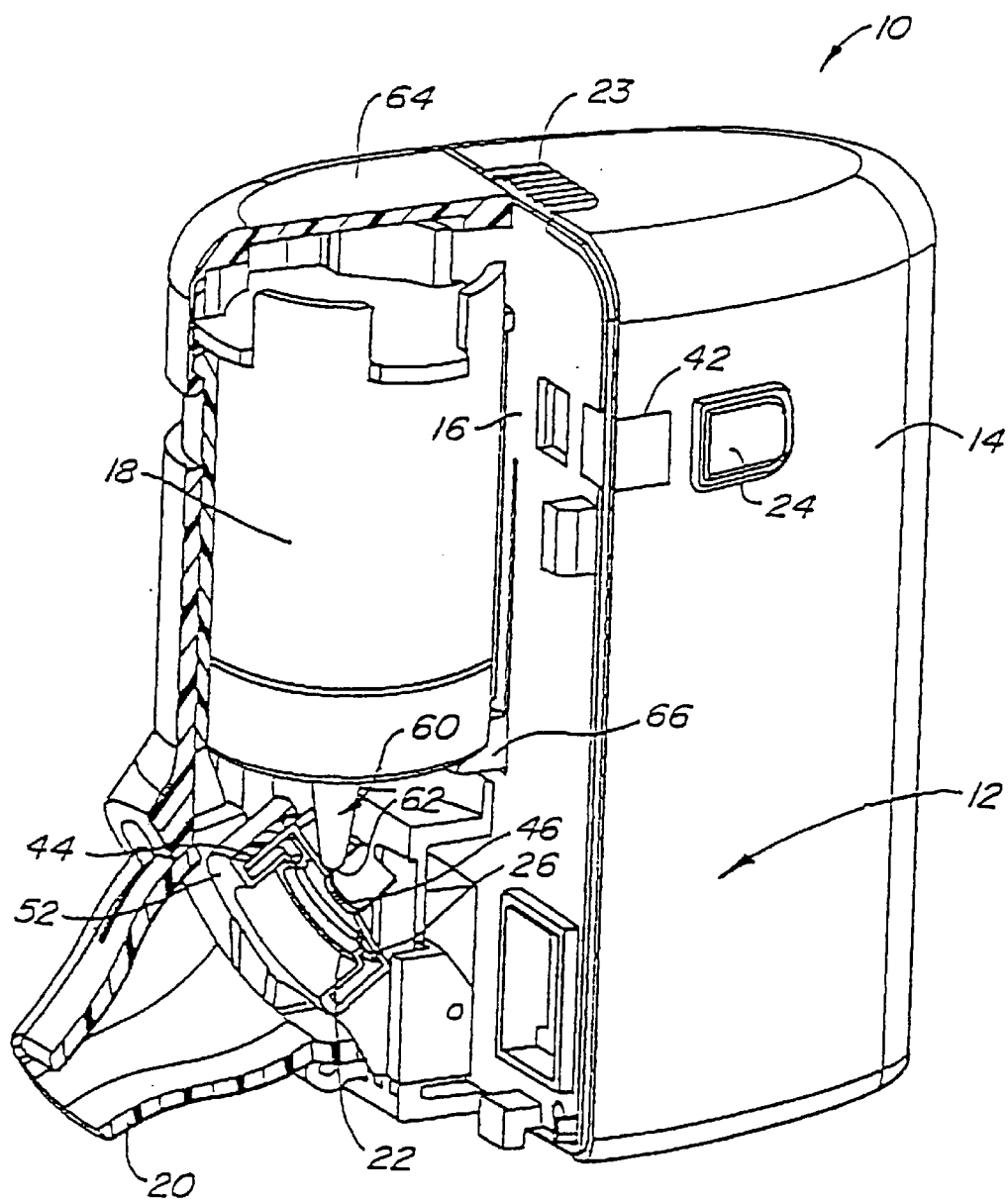

Another feature of the liquid dispensers of the invention is that they are configured to prevent or substantially reduce the possibility of contamination. In this way, each subsequent dosage delivered by the liquid dispenser is not contaminated when delivered to the atomizer. Referring now to FIG. 1, an exemplary apparatus 10 for atomizing a liquid will be described. Apparatus 10 comprises a housing 12 which is configured to hold the various components of apparatus 10. Housing 12 is preferably constructed to be lightweight and pocket-sized, typically being molded of a plastic material. Housing 12 is divided into two separable portions. A first portion 14 includes an electronics compartment and a second portion 16 includes a liquid holding compartment for holding a canister 18, an aerosol generator 22, and a mouthpiece 20 through which the atomized liquids are dispensed to the patient. Conveniently, second portion can be separated from first portion 14 by sliding a knob 23. Optionally, second portion 16 having the liquid holding component may be disposed following separation from first portion 14. Second portion 16 may be disposed along with canister 18, or canister 18 may be disposed separately.

Apparatus 10 further includes an inhalation flow sensor 24 which detects the inhalation flow produced by the patient when inhaling from mouthpiece 22. Upon detection of the inhalation, sensor 24 sends an electrical signal to an electronic circuit (not shown) which in turn sends an alternating voltage to vibrate a piezoelectric member 26 of aerosol generator 22 to aerosolize a liquid. Sensor 24 preferably comprises a flexure foil and an electro-optical sensor. The flexible foil deflects in response to the inhalation airflow produced when a patient inhales from mouthpiece 20. The optical sensor is configured to detect deflection of the flexible foil so that a signal may be produced to vibrate piezoelectric member 26.

Figure 2:
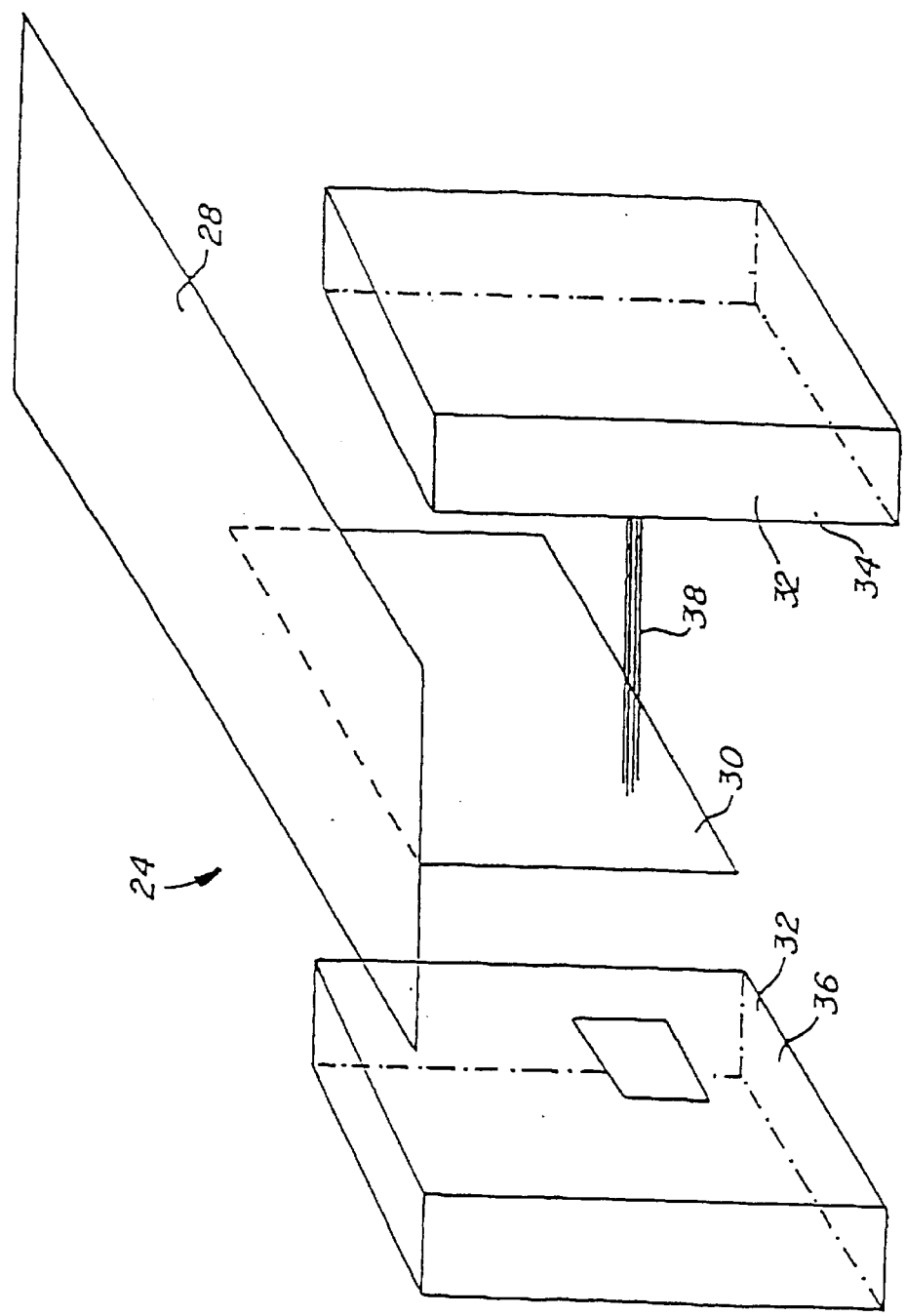

Referring now to FIG. 2, a schematic diagram of an inhalation flow sensor 24 will be described. Flow sensor 24 comprises a flexible foil 28 having an extension 30. Inhalation flow sensor 24 further includes an optical sensor 32 which includes a light emitting diode (LED) 34 and a light sensitive transistor 36 placed in apposition to LED 34 so that LED 34 continuously transmits a light beam 38 to transistor 36. When the patient inhales, the inhalation airflow causes flexible foil 28 to deflect and move extension 30 downward until it crosses light beam 38 and causes an optical interruption that is detected by transistor 36. Transistor 36 then sends a signal to trigger activation of an aerosol generator to produce an aerosol.

By configuring inhalation flow sensor 24 in this manner, aerosol generator 22 is actuated only in response to the detection of an inhalation airflow produced by a patient. In this way, the patient may be administered a single dose using either a single inhalation or multiple inhalations. Preferably, inhalation flow sensor 24 is triggered at an inhalation flow rate of at least 15 liters per minute. However, it will be appreciated that sensor 24 may be constructed to trigger at either lower or higher flow rates. Adjustment of the actuation point may be accomplished by altering the flexible stiffness of foil 28, by selecting different materials for constructing foil 28 or by changing the thickness of foil 28.

Alternatively, the inhalation flow sensor may be constructed from a piezoelectric film component. The piezoelectric film component produces an electrical signal when it deflects. The magnitude of the electrical signal is proportional to the magnitude of deflection. In this way, the electrical signal that is produced by the piezoelectric film component can be used to detect the magnitude of the inhalation flow. In this manner, the output of the aerosol generator may be adjusted in proportion to the inhalation airflow. Such a proportional output from the aerosol generator is particularly advantageous in that it prevents the coalescence of particles and controls the aerosol production according to the inhalation flow. Control of the aerosol output may be adjusted by turning the aerosol generator on and off sequentially. The ratio between the on time and the off time, generally defined as the duty cycle, affects the net flow. An exemplary piezoelectric film component with such characteristics is commercially available from ATO Autochem Sensors, Inc., Valley Forge, Pa.

Referring back to FIG. 1, the electronic circuit (not shown) within first portion 14 includes electrical components to detect the presence of liquid on aerosol generator 22 and to send a signal to the user indicating that all of the liquid has been aerosolized. In this way, the user will know if additional inhalations will be required in order to receive the prescribed amount of medicament. The sensing circuit preferably comprises a voltage sensing circuit (not shown) which detects the voltage across piezoelectric element member 26. Since the voltage across piezoelectric member 26 is proportionally related to the amount of liquid in surface tension contact with an aperture plate 40 (see FIG. 3) of aerosol generator 22, it can be determined, based on the voltage, whether any liquid is left remaining. For example, when aerosolization is initiated, the voltage is high. At the end of aerosolization, the voltage is low, thereby indicating that the aerosolization process is near completion. Preferably, the sensing circuit is configured to be triggered when about 95% of the liquid has been aerosolized. When triggered, the sensing circuit turns on a light emitting diode (LED) 42 indicating that the prescribed dosage has been delivered.

Figure 3:
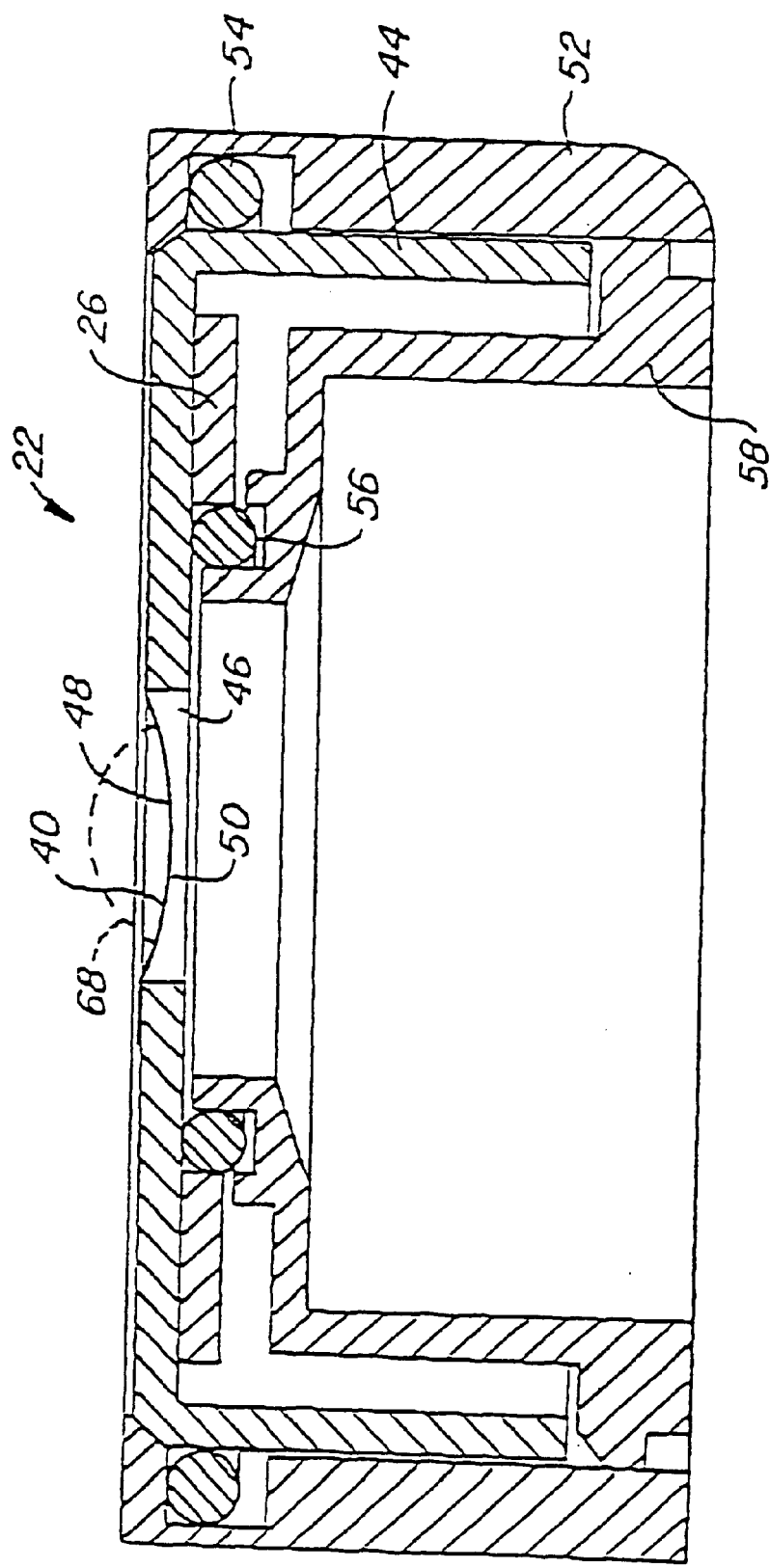
Figure 4:
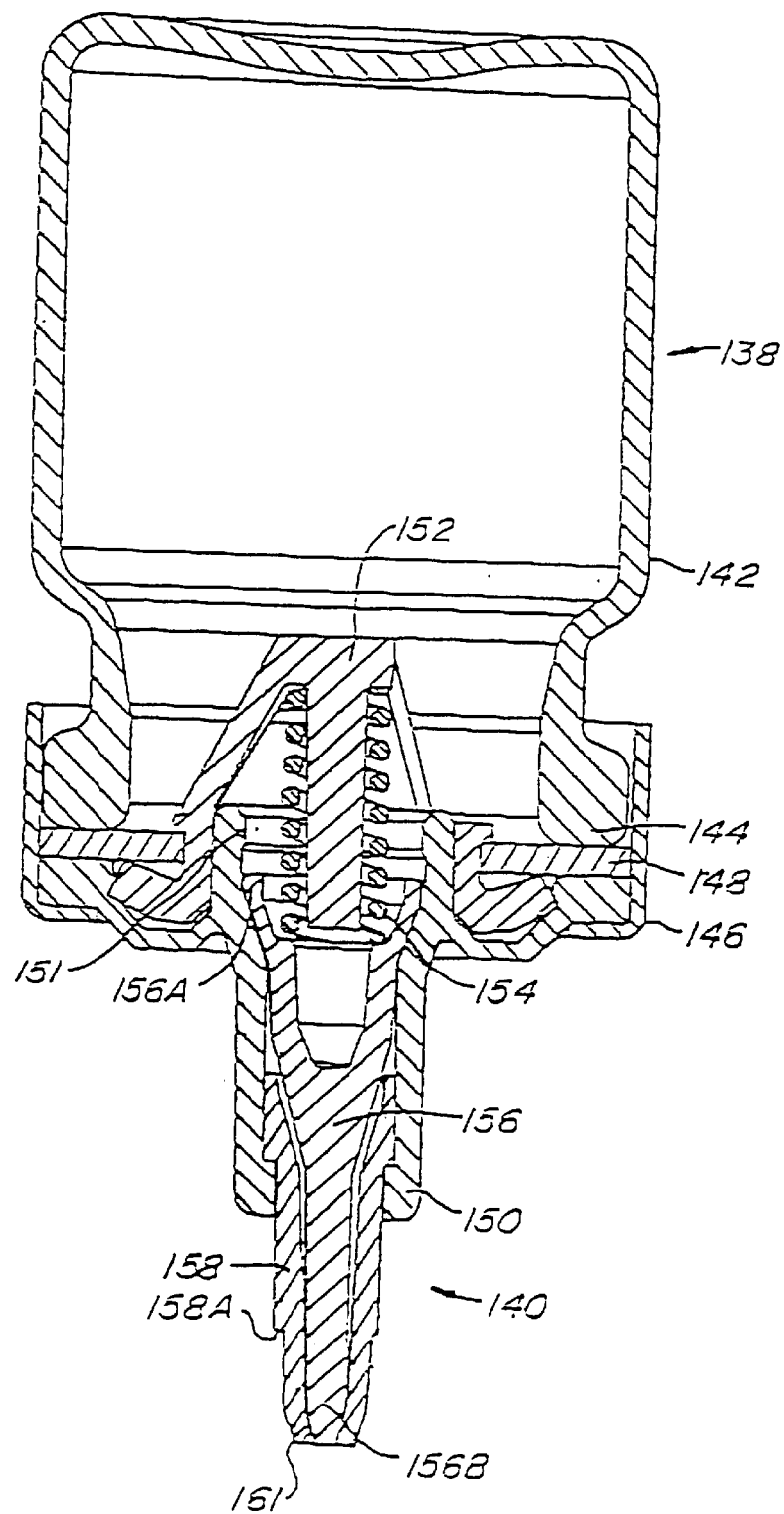
Figure 5:
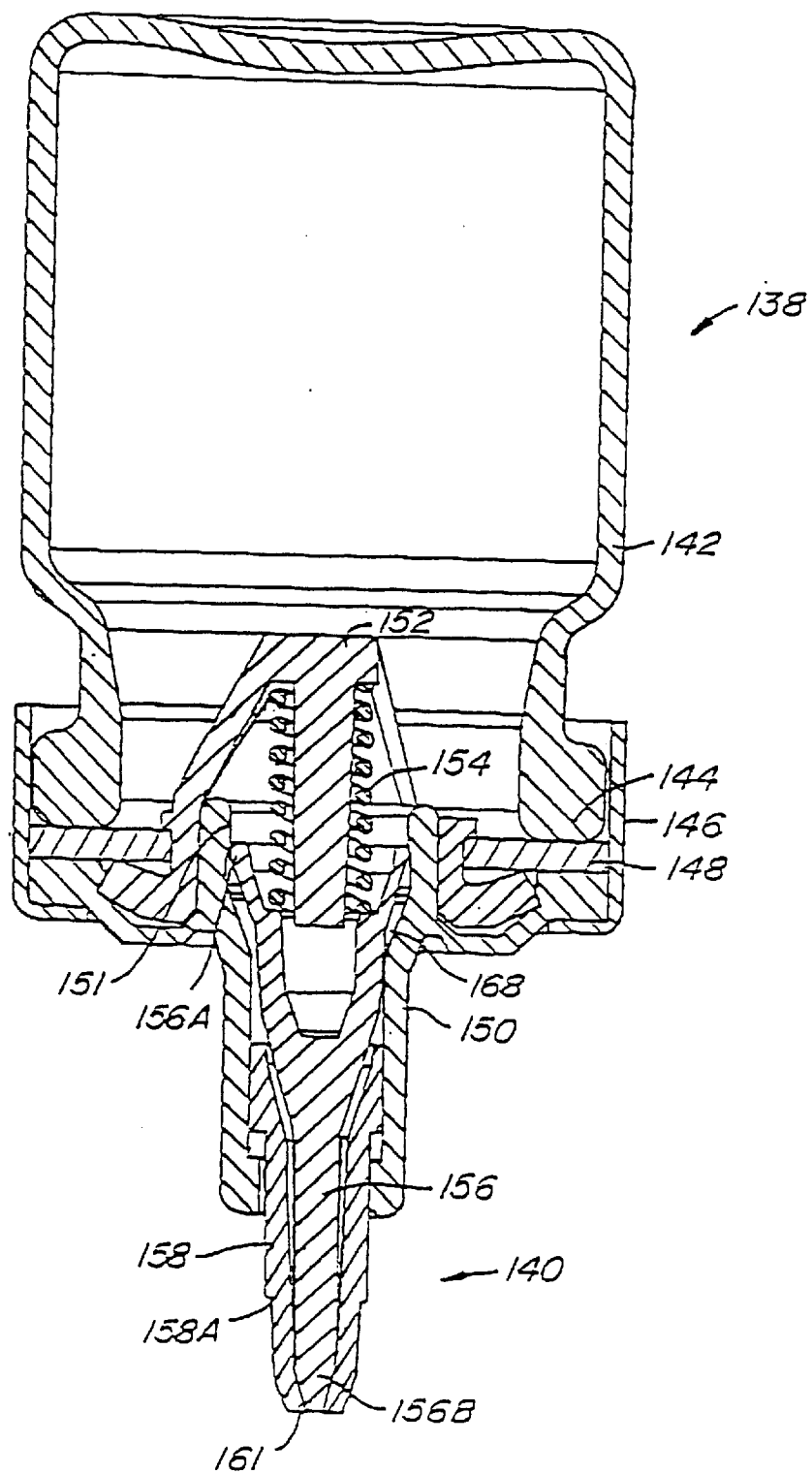
Figure 6:
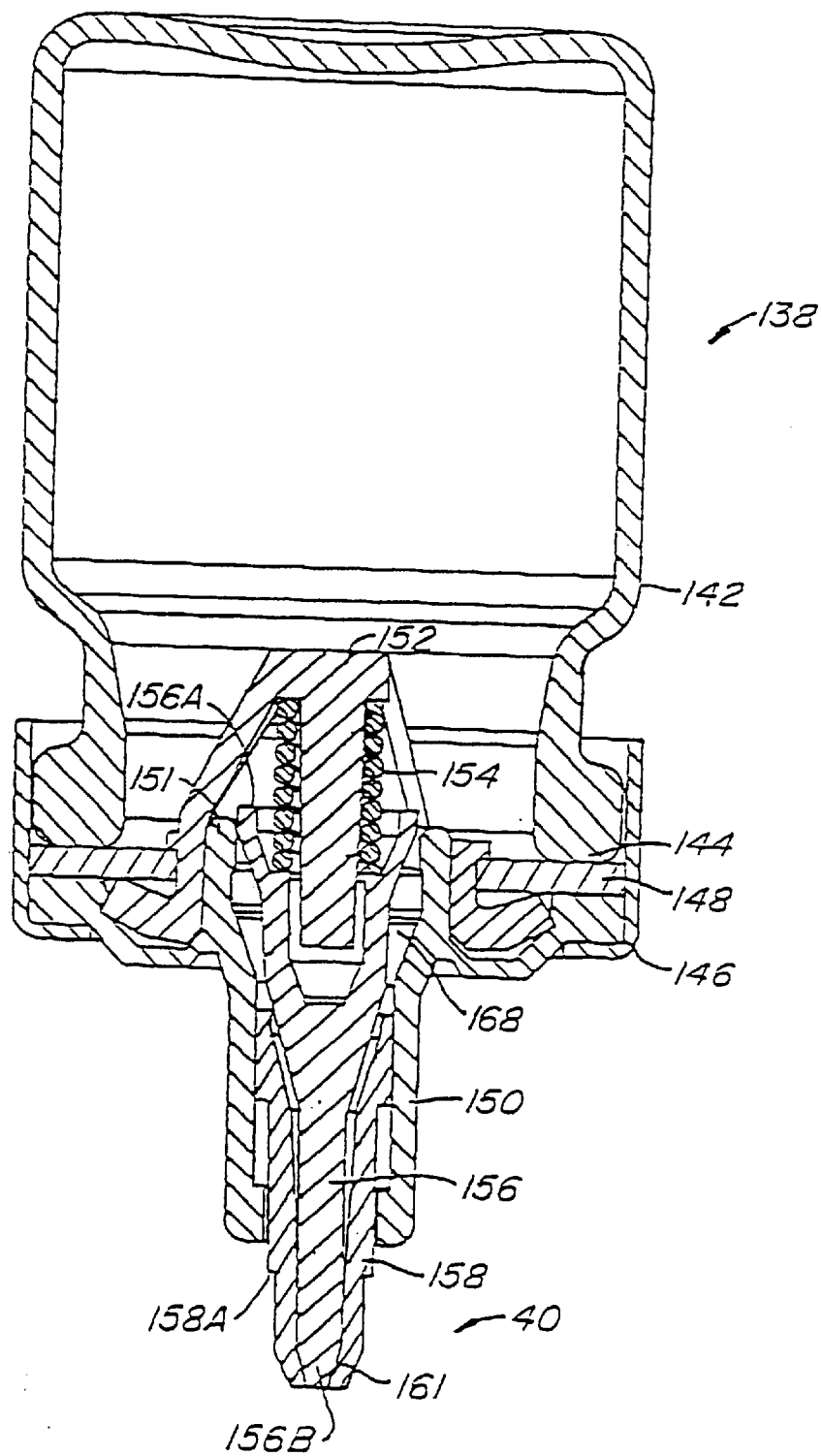
Figure 7:
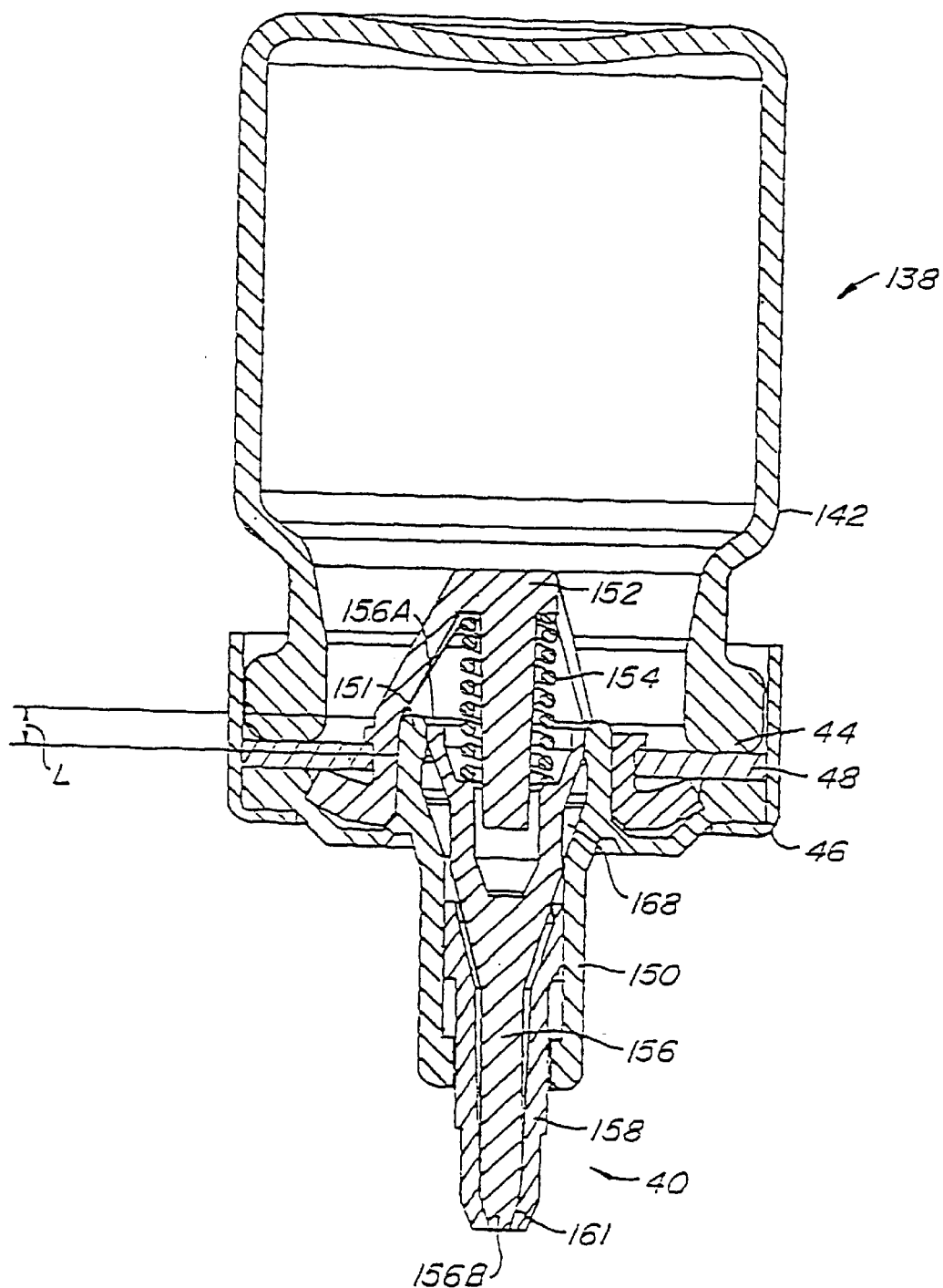
Figure 8:
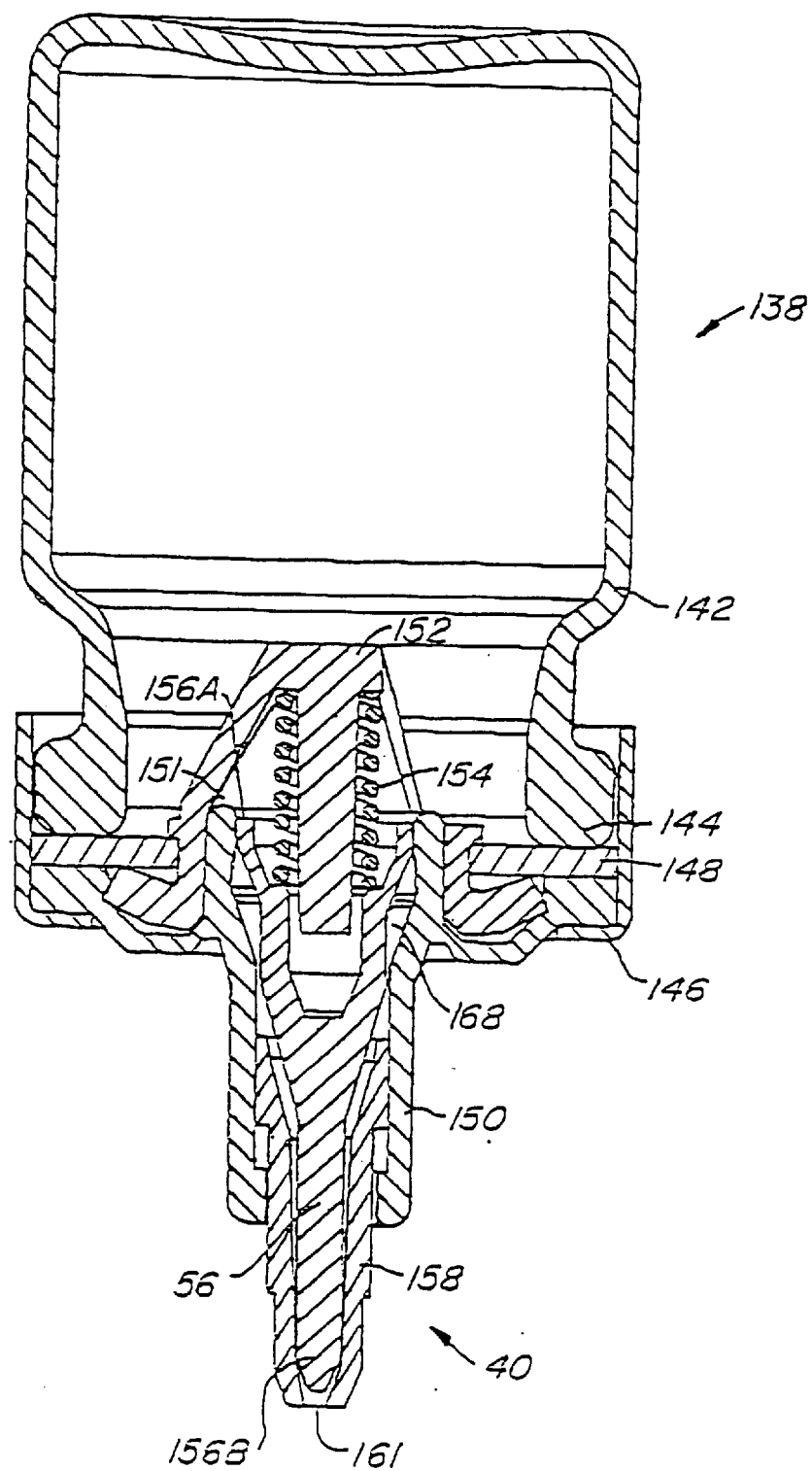
Figure 9:
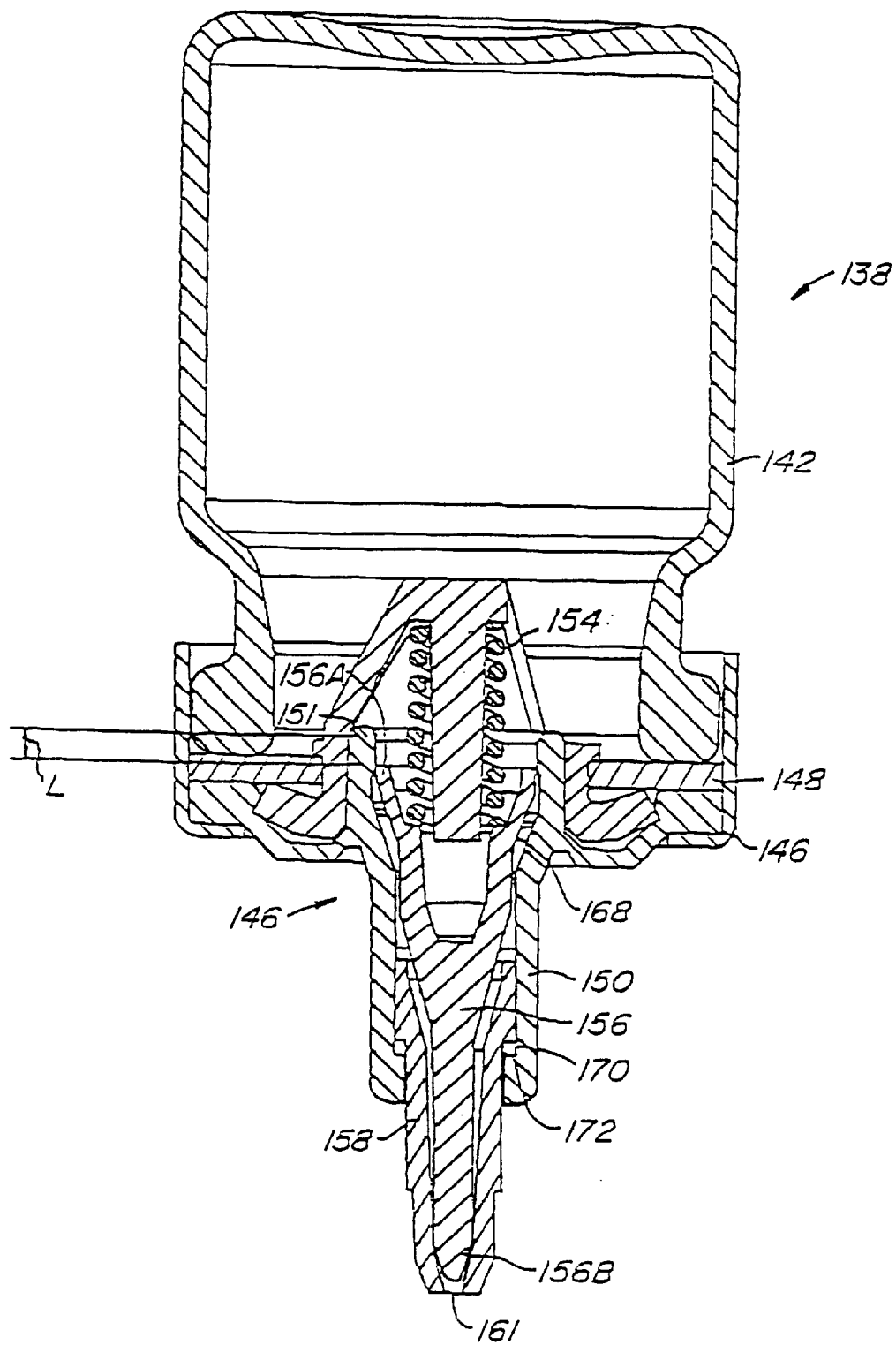
Figure 10:
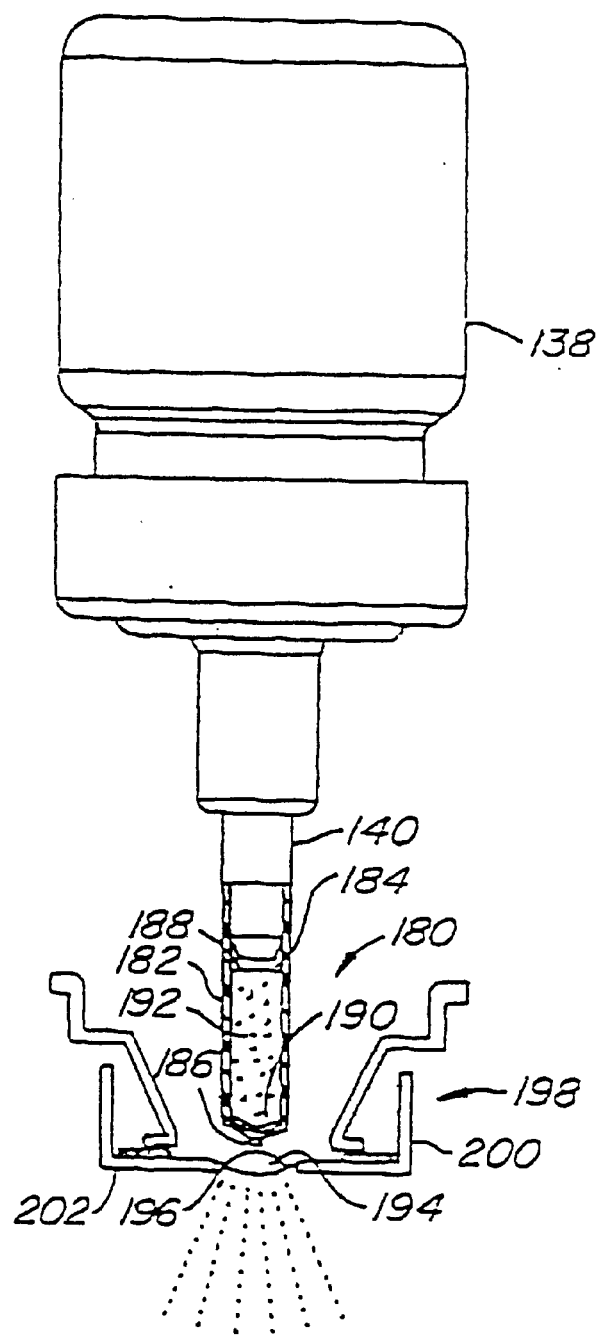

Referring now to FIG. 3, construction of aerosol generator 22 will be described in greater detail. As previously described, aerosol generator 22 includes a vibratable aperture plate 40 and annular piezoelectric member 26. Aerosol generator 22 further comprises a cup-shaped member 44 to which piezoelectric member 26 and aperture plate 40 are attached as shown. Cup-shaped member 44 includes a circular hole 46 over which aperture plate 40 is disposed. Wires (not shown) connect piezoelectric member 26 to the electrical circuitry within portion 14 (see FIG. 1) which in turn is employed to vibrate piezoelectric member 26.

Cup-shaped member 44 is preferably constructed of a low damping metal, such as aluminum. Aperture plate 40 is disposed over hole 46 such that a rear surface 48 of aperture plate 40 is disposed to receive liquid from canister 18 (see FIG. 1). Although not shown, aperture plate 40 includes a plurality of tapered apertures which taper from rear surface 48 to a front surface 50. Exemplary aperture plates which may be used with the invention include those described the '740 patent, the '550 patent, and the '637 patent, previously incorporated by reference.

Aperture plate 40 is preferably constructed of a material that may be produced by a metal electroforming process. As an example, aperture plate 40 may be electroformed from palladium or a palladium alloy, such as palladium cobalt or palladium nickel. Aperture plate 40 may further be gold electroplated to enhance its corrosion resistance. Alternatively, aperture plate 40 may be constructed of nickel, a nickel-gold alloy, or a combination of nickel and nickel-gold alloy arranged such that the nickel-gold alloy covers the external surfaces of the aperture plate. The nickel-gold alloy may be formed using a gold electroplating process followed by diffusion at an elevated temperature as described generally in Van Den Belt, TGM, "The diffusion of platinum and gold in nickel measured by Rutherford Fact Scattering Spectrometry", Thin Solid Film, 109 (1983), pp. 1–10. The complete disclosure of this reference is incorporated herein by reference. A small amount of manganese may also be introduced to the nickel during the electroforming process so that the nickel can be heat treated at an elevated temperature as described generally in U.S. Pat. No. 4,108,740, incorporated herein by reference. The gold-nickel alloy is particularly useful in protecting the nickel components, and particularly the electroformed nickel components, from corrosion caused by plating porosity. The diffusion process may be useful for other applications which require corrosion protection for nickel components, and particularly nickel electro formed components, such as, for example, inkjet aperture plates, other spray nozzle plates, and the like.

As another alternative, corrosion resistance of the aperture plate may be enhanced by constructing the aperture plate of a composite electro formed structure having two layers, with the first electro formed layer comprising nickel and the second electro formed layer comprising gold. The thickness of the gold in the composite in preferably at least two microns, and more preferably, at least five microns. Alternatively, the second layer may be electro formed from palladium or another corrosive-resistant metal. The external surfaces of the aperture plate may also be coated with a material that prevents bacteria growth, such as polymyxin or silver. Optionally, other coatings that enhance wetability may be applied to the aperture plate.

In one embodiment, the aperture plate is protected from corrosive liquids by coating the aperture plate with agents that form a covalent bond with the solid surface via a chemical linking moiety. Such agents are preferred because the are typically biocompatable with acidic pharmaceutical liquids. The agent may be photoreactive, i.e. activated when subjected to light or may be activated when subjected to moisture or to any other means of energy. Further, the agent may have various surface properties, e.g. hydrophobic, hydrophilic, electrically conductive or non-conductive. Still further, more than one agent may be formed on top of each other. Types of coatings that may be included on the aperture plate are described in U.S. Pat. Nos. 4,979,959; 4,722,906; 4,826,759; 4,973,493; 5,002,582; 5,073,484; 5,217,492; 5,258,041; 5,263,992; 5,414,075; 5,512,329; 5,714,360; 5,512,474; 5,563,056; 5,637,460; 5,654,460; 5,654,162; 5,707,818; 5,714,551; and 5,744,515. The complete disclosures of all these patents are herein incorporated by reference.

Cup-shaped member 44 is disposed within a housing 52 which prevents liquids from coming into contact with piezoelectric member 26 and with cup-shaped member 44. Cup-shaped member 44 is suspended within housing 52 by two elastic rings 54 and 56. Ring 54 is positioned between housing 52 and the circumference of cup-shaped member 44. Ring 56 is positioned between the inner diameter of piezoelectric member 26 and a shield member 58. Such an arrangement provides a hermetic seal that prevents the contact of liquids with the piezoelectric member 26 without suppressing the vibratory motion of cup-shaped member 44.

Referring back now to FIG. 1, aerosol generator 22 is axially aligned with mouthpiece 20 so that when piezoelectric member 26 is vibrated, liquid droplets are ejected through mouthpiece 20 and are available for inhalation by the patient. As previously described, disposed within second portion 16 is a canister 18 which holds the liquid medicament to be atomized by aerosol generator 22. Canister 18 is integrally attached to a mechanical pump 60 which is configured to dispense a unit volume of liquid through a nozzle 62 to aerosol generator 22. Pump 60 is actuated by pressing a knob 64 which pushes canister 18 downward to generate the pumping action as described in greater detail hereinafter. Pressing on knob 64 also puts pressure on an electrical microswitch 66 within second portion 16. When actuated, microswitch 66 sends a signal to the electrical circuit within first portion 14 causing a light emitting diode (LED) (not shown) to blink indicating that apparatus 10 is ready for use. When the patient begins to inhale, the inhalation is sensed causing actuation of the aerosol generator.

As illustrated in FIG. 3, pump 60 delivers a unit volume of liquid 68 (shown in phantom line) to rear surface 48 of aperture plate 40. The delivered volume 68 adheres to aperture plate 40 by solid/liquid surface interaction and by surface tension forces until patient inhalation is sensed. At that point, piezoelectric member 26 is actuated to eject liquid droplets from front surface 50 where they are inhaled by the patient. By providing the delivered volume 60 in a unit volume amount, a precise dose of liquid medicament may be atomized and delivered to the lungs of the patient. Although canister 18 of FIG. 1 is shown as being configured to directly deliver the dispensed liquid to the aperture plate, pump 60 may alternatively be configured to receive a cartridge containing a chemical in a dry state as described in greater detail hereinafter.

Referring now to FIGS. 4–10, a schematic representation of a canister 138 and a piston pump 140 will be described to illustrate an exemplary method for dispensing a unit volume of a liquid medicament to an aperture plate, such as aperture plate 40 of apparatus 10 (see FIGS. 1 and 3). Canister 138 comprises a housing 142 having an open end 144 about which a cap 146 is placed. Disposed against open end 144 is a washer 148 which provides a seal to prevent liquids from escaping from housing 142. On top of washer 148 is a cylindrical member 150. Cap 146 securely holds cylindrical member 150 and washer 148 to housing 142. Cylindrical member 150 includes a cylindrical opening 151 which allows liquids to enter from canister 138. Cylindrical member 150 in combination with washer 148 also serve to securely position a holding member 152 about which a compression spring 154 is disposed.

Piston pump 140 comprises a piston member 156, cylindrical member 150, a valve seat 158 and compression spring 154. Piston member 156 has a frontal end 156A and a distal end 156B, with frontal end 156A providing the piston action and distal end 156B providing the valve action.

Piston pump 140 is configured such that every time valve seat 158 is depressed toward canister 138 and then released, a unit volume of liquid is dispensed through a tapered opening 161 in valve seat 158. Valve seat 158 includes a valve seat shoulder 158A which is pressed to move valve seat inwardly, causing valve seat 158 to engage with distal end 156B to close tapered opening 161.

As shown in FIG. 5, as piston member 156 is further depressed into cylindrical member 150, spring 154 is compressed and a metering chamber 168 begins to form between frontal end 156A and cylindrical member 150. Frontal end 156A and distal end 156B are preferably constructed from a soft elastic material which provides a hermetic seal with cylindrical member 150 and valve seat 158, respectively. Due to the seal between frontal end 156A and cylindrical member 150, a vacuum is created within metering chamber 168 upon depression of piston member 156.

As piston member 156 is further moved into cylindrical member 150 (see FIG. 6), spring 154 is further compressed and frontal end 156A moves past cylindrical opening 151 so that a gap is provided between frontal end 156A and cylindrical member 150. As frontal end 156A passes the edge of cylindrical member 150, liquid from canister 138 is drawn into cylindrical member 150 by the vacuum that was created within metering chamber 168. In FIG. 6, piston member 156 is in the filling position.

At the end of inward travel, the user releases the pressure on valve seat 158, allowing spring 154 to push piston member 156 back toward its starting position. As illustrated in FIG. 7, upon the return travel of piston member 156 to the starting position, frontal end 156A again engages cylindrical member 150 and forms a seal between the two surfaces to prevent any liquid within metering chamber 168 from flowing back into canister 138.

Since the liquid within metering chamber 168 is generally incompressible, as spring 154 pushes on piston member 156, the liquid within metering chamber 168 forces valve seat 158 to slide distally over piston member 156. In so doing, the liquid within metering chamber 168 is allowed to escape from the metering chamber through tapered opening 161 of valve seat 158 as illustrated in FIG. 8.

As illustrated in FIGS. 7–9, liquid from metering chamber 168 is dispensed from tapered opening 161 as frontal end 156A travels length L. As frontal end 156A passes through length L, it is in contact with cylindrical member 150. In this way, the liquid within metering chamber 168 is forced out of tapered opening 161 during this length of travel. After passing through Length L, frontal end 156A passes out of sealing relationship with cylindrical member 150 so that no further liquid is dispensed from tapered opening 161. Hence, the amount of liquid dispensed is proportional to the diameter of cylindrical member 150 over length L. As such, piston pump 140 may be designed to dispense a known volume of liquid each time piston member 156 travels from the starting position to the filling position and then back to the starting position. Since piston member 156 must be fully depressed to the filling position in order to create a gap between frontal end 156A and cylindrical member 150, a way is provided to ensure that partial volumes can not be dispensed.

As shown in FIG. 9, valve seat 158 includes a shoulder 170 which engages a stop 172 on cylindrical member 150 to stop distal movement of valve seat 158 relative to cylindrical member 150. At this point, piston pump 140 is at an ending dispensing position which corresponds to the starting position as initially illustrated in FIG. 4. In this position, spring 154 forces distal end 156B of piston member 156 into tapered opening 161 to provide a seal and prevent contaminants from entering into piston 140.

Valve seat 158 is preferably coated with a material that inhibits proliferation of bacteria. Such coatings can include, for example, coatings having a positive electric charge, such as polymyxin, polyethylinimin, silver, or the like.

The invention further provides a convenient way to store chemical substances in the solid or dry state and then to dissolve the chemical substance with liquid from the canister to form a solution. In this way, chemical substances that are otherwise susceptible to degradation can be stored in the dry state so that the shelf life of the product is extended. An exemplary embodiment of a cartridge 180 for storing such chemical substances that are in the dry state is illustrated in FIG. 10. For convenience of illustration, cartridge 180 will be described in connection with piston pump 140 and canister 138, which in turn may be coupled to an aerosolization apparatus, such as apparatus 10, to aerosolize a medicament as previously described. Cartridge 180 comprises a cylindrical container 182 having an inlet opening 184 and outlet opening 186. Inlet opening 182 is sized to be coupled to piston pump 140 as shown. Disposed within container 182 is a first filter 188 and a second filter 190. Filter 188 is disposed near inlet opening 184 and second filter 190 is disposed near outlet opening 186. A chemical substance 192 which is in a dry state is disposed between filters 188 and 190. Chemical substance 192 is preferably held within a support structure to increase the rate in which the chemical substance is dissolved.

The support structure may be constructed of a variety of materials which are provided to increase the rate in which the chemical substance is dissolved. For example, the support structure may comprise an open cell material such as a polytetrafluoroethylene (PTFE) matrix material commercially available from Porex Technologies, Farburn, Ga. Preferably, such an open cell material has a pore size in the range from about 7 $\mu$m to about 500 $\mu$m, and more preferably about 250 $\mu$m. Alternatively, various other plastic materials may be used to construct the open cell matrix, including olyethylene (HDPE), ultra-high molecular weight polyethylene (UHMW), polypropylene (PP), polyvinylidene fluoride (PVDF), nylon 6 (N6), polyethersulfone (PES), ethyl vinyl acetate (EVA), and the like. Alternatively, the support structure may be constructed of a woven synthetic material, a metal screen, a stack of solid glass or plastic beads, and the like.

An exemplary method for placing chemical substance 192 into container 182 is by filling container 182 with the chemical substance while the chemical substance is in a liquid state and then lyophilizing the substance to a dry state while the substance within the cartridge. In this way, filling of cartridge 180 with a chemical substance may be precisely and repeatedly controlled. However, it will be appreciated that the chemical substance may be placed into cartridge 180 when in the solid state.

Lyophilization is one exemplary process because it will tend to reduce the rate of various physical and chemical degradation pathways. If the substance comprises a protein or peptide, both the lyophilization cycle (and resulting moisture content) and product formulation can be optimized during product development to stabilize the protein before freezing, drying and for long term storage. See Freeze Drying of Proteins, M. J. Pikal, BioPharm. 3, 18–26 (1990); Moisture Induced Aggregation of Lyophilized Proteins in the Solid State, W. R. Liu, R. Langer, A. M. Klibanov, Biotech. Bioeng. 37, 177–184 (1991); Freeze Drying of Proteins. II, M. J. Pikal, BioPharm. 3, 26–30 (1990); Dehydration Induced Conformational Transitions in Proteins and Their Inhibition by Stabilizers, S. J. Prestrelski, N. Tedeschi, S. Arakawa, and J. F. Carpenter, Biophys. J. 65, 661–671 (1993); and Separation of Freezing and Drying Induced Denaturation of Lyophilized Proteins Using Stress-Specific Stabilization, J. F. Carpenter, S. J. Prestrelski, and T. Arakawa, Arch. Biochem. Biphys. 303, 456–464 (1993), the complete disclosures of which are herein incorporated by reference. Adjustment of the formulation pH and/or addition of a wide variety of additives including sugars, polysaccharides, polyoles, amino-acids, methylamines, certain salts, as well as other additives, have been shown to stabilize protein towards lyophilization.

As an example, which is not meant to be limiting, a cartridge was packed with small glass beads having a diameter of approximately 0.5 mm. The cartridge was filed with a solution of lysozyme at a concentration of 10 mg/ml. To enhance its stability, the solution was combined with a form of sugar and with a buffer solution. The buffer solution was sodium citrate, and the sugar was mannitol. A twin 20 surfactant was also added to the solution. The solution was then lyophilized in the cartridge.

The lyophilized substance may optionally contain a solubility enhancer, such as a surfactant as described in Journal of Pharmaceutical Science Technology which is J.Pharmsei. Technology, 48; 30–37 (1994) the disclosure of which is herein incorporated by reference. To assist in protecting the chemical substance from destructive reactions while in the dry state, various sugars may be added as described in Crowe, et al., "Stabilization of Dry Phospholipid Bilayer and Proteins by Sugars", Bichem. J. 242: 1–10 (1987), and Carpenter, et al. "Stabilization of Phosphofructokinase with Sugars Drying Freeze-Drying", Biochemica. et Biophysica Acta 923: 109–115 (1987), the disclosures of which are herein incorporated by reference.

In use, cartridge 180 is coupled to piston pump 140 and piston pump 140 is operated as previously described to dispense a known volume of liquid into cartridge 180. The supplied liquid flows through chemical substance 192 and chemical substance 192 dissolves into the liquid and flows out of outlet opening 186 as a liquid solution 194. Outlet opening 186 is spaced apart from an aperture plate 196 of an aerosol generator 198 so that liquid solution 198 will be deposited on aperture plate 196 as shown. Aerosol generator 198 further includes a cup shaped number 200 and a piezoelectric member 202 and operates in a manner similar to the aerosol generator 22 as previously described. Hence, when aerosol generator 198 is operated, liquid solution 194 is ejected from aperture plate 196 in droplet form as shown.

Figure 11:
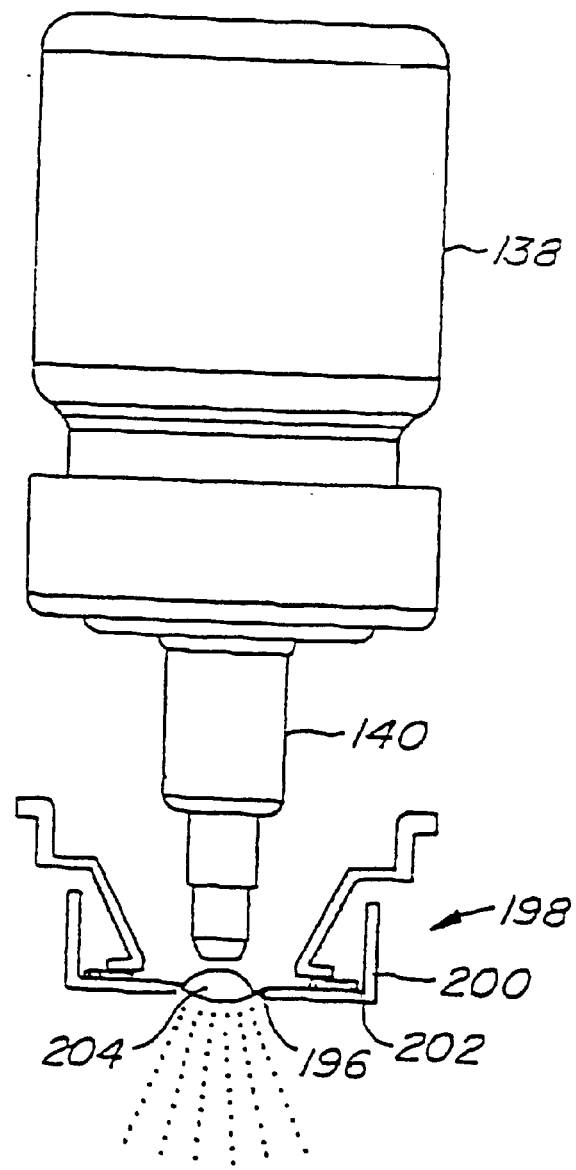

One important feature of the invention is that cartridge 180 is removable from piston pump 140 so that cartridge 180 may be discarded following each use. As illustrated in FIG. 11, after cartridge 180 has been removed, the user may optionally actuate piston pump 140 to again deliver a volume of liquid 204 directly to aperture plate 96. Aerosol generator 198 is then operated so that, similar to an ultrasonic cleaner, the vibratory action removes any residual solution from aperture plate 196. Liquids that may be held within canister 138 to form the solution and to clean aperture plate 196 include sterile water, a mixture of water with ethanol or other disinfectant, and the like.

In summary, the invention provides a portable aerosolizing apparatus that is able to store a chemical substance in the dry state, and to reconstitute the chemical substance with liquid to form a solution just prior to administration. The invention further provides techniques for aerosolizing the solution and for cleaning the aerosol generator. Also, it will be appreciated that the aerosolization apparatus as described herein may be used to aerosolize a liquid medicament that is not stored within a cartridge so that the liquid medicament is passed directly from the piston pump and on to the aperture plate for aerosolization.

Apparatus 10 may optionally be configured to warn the user when cleaning is needed. Such a feature is best accomplished by providing a processor within second portion 14 which is programmed to include an expected amount of time required to aerosolize a dose received from canister 18. If the expected amount of time exceeded before the entire dose is aerosolized, it may be assumed that the apertures in the aperture plate are clogged, thereby requiring cleaning to clear the apertures. In such an event, the processor sends a signal to an LED on apparatus 10 indicating that cleaning is needed.

To determine whether all of the liquid has been aerosolized in the expected time period, the processor records the amount of time that the aerosol generator is actuated. When the aerosol generator has been actuated for the expected time, the voltage sensing circuit is actuated to detect whether any liquid remains on the aperture plate as previously described.

Figure 12:
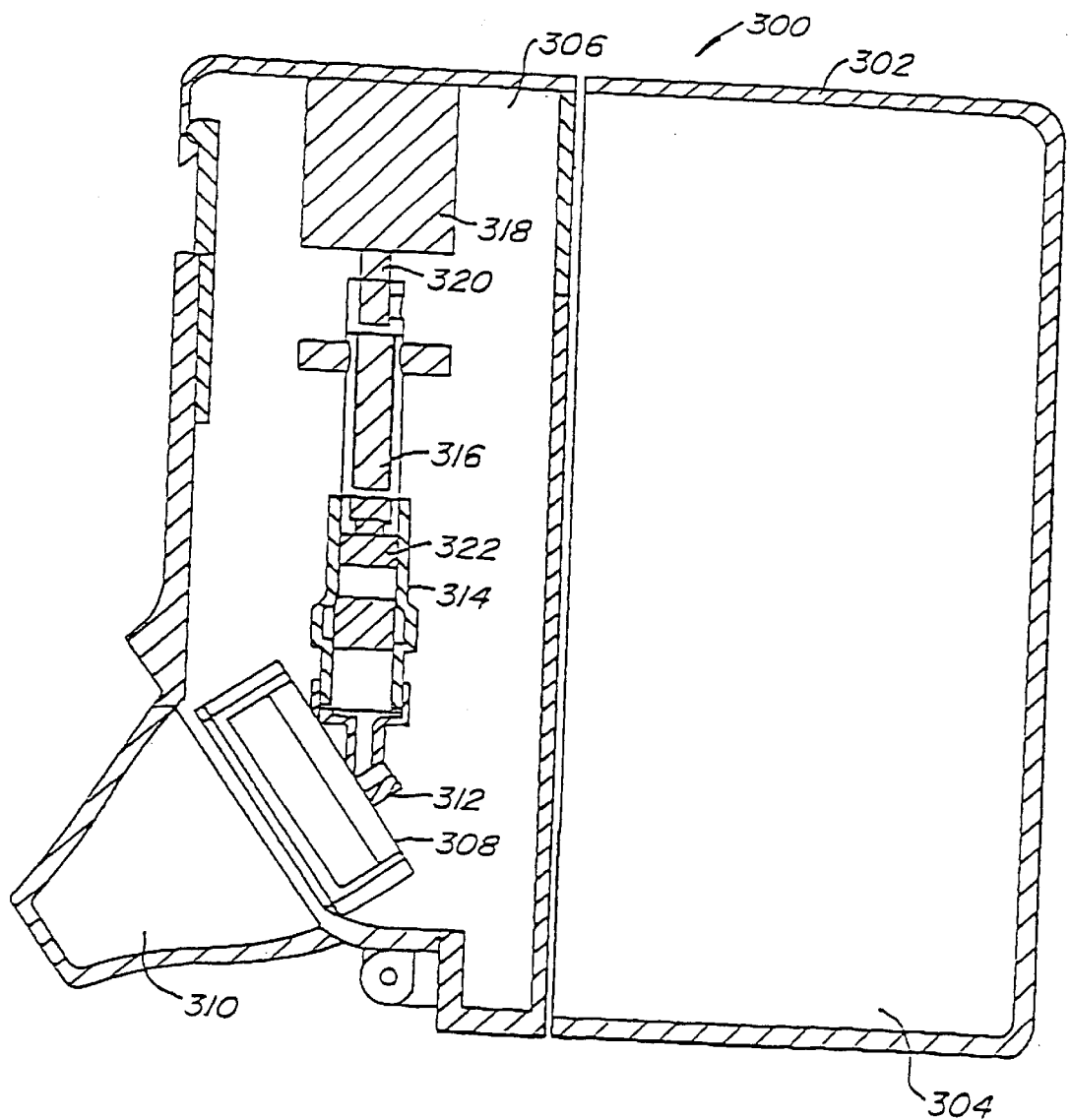

Referring now to FIG. 12, an alternative embodiment of an apparatus 300 for atomizing a liquid solution will be described. Apparatus 300 includes a housing 302 that is divided into two separable portions similar to the embodiment of FIG. 1. A first portion 304 includes various electronics and a second portion 306 includes a liquid holding compartment. An aerosol generator 308 which is similar to aerosol generator 22 of FIG. 1 is disposed in second portion 306 to aerosolize a solution where it will be available for inhalation through a mouthpiece 310. Conveniently, aerosol generator 308 includes a lip 312 to catch the solution and maintain it in contact with the aerosol generator 308 until aerosolized. Disposed above aerosol generator 308 is a drug cartridge 314. As will be described in greater detail hereinafter, cartridge 314 is employed to produce a solution which is delivered to aerosol generator 308 for aerosolization.

Coupled to cartridge 314 is a lead screw 316. In turn, lead screw 316 is coupled to a micro-coreless DC motor 318. When motor 318 is actuated, it causes a shaft 320 to rotate. This rotational motion is converted to linear motion by lead screw 316 to translate a piston 322 within cartridge 314 as described in greater detail hereinafter. Motor 318 is actuated by appropriate electronics held in first portion 304. Further, a power source, such as a battery, is also held within first portion 304 to supply power to motor 318. Aerosol generator 38 is operated in a manner essentially identical to that previously described in connection with the apparatus of FIG. 1.

Figure 13:
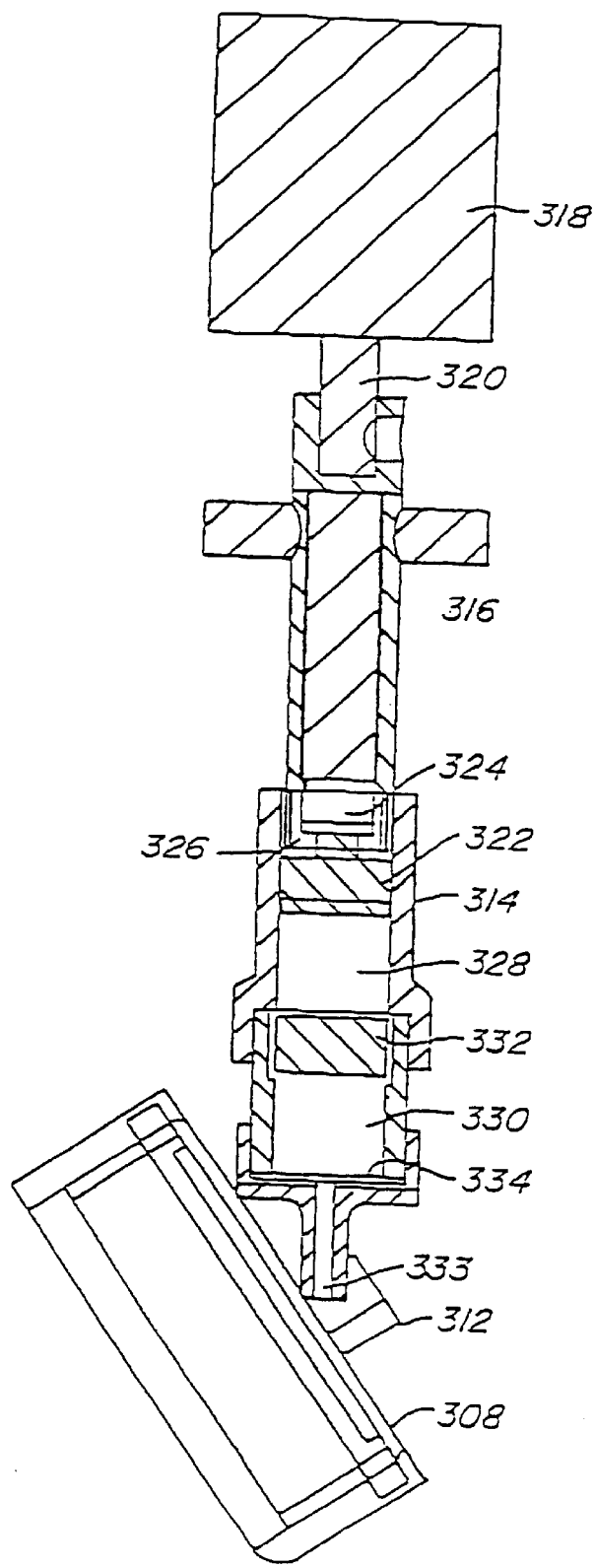

Referring now to FIG. 13, construction of cartridge 314 will be described in greater detail. Piston 322 includes a docking knob 324 which mates with a connector 326 of lead screw 316. Docking knob 324 and connector 326 are configured to facilitate easy coupling and uncoupling. Typically, motor 318 and lead screw 316 are securely coupled to housing 308 (see FIG. 12), while cartridge 314 is configured to be removable from housing 302. In this way, each time a new drug cartridge is required, it may be easily inserted into apparatus 300 and coupled with lead screw 316.

Lead screw 316 is configured such that when motor 318 causes shaft 320 to rotate in a clockwise direction, lead screw 316 is moved downward. Alternatively, when motor 318 is reversed, lead screw 316 is moved upward. In this way, piston 322 may be translated back and forth within cartridge 314. Motor 318 is preferably calibrated such that piston 322 can be moved to selected positions within cartridge 314 as described in greater detail hereinafter.

Cartridge 314 includes a first chamber 328 and a second chamber 330. Although not shown for convenience of illustration, first chamber 328 is filled with a liquid and second chamber 330 includes a substance that is in a dry state. Such a substance preferably comprises a lyophilized drug, although other substances may be employed similar to the embodiment of FIG. 1. Separating first chamber 328 and second chamber 330 is a divider 332. As shown in FIG. 13, divider 332 is in a home position which forms a seal between divider 332 and cartridge 314 so that the liquid is maintained within first chamber 328 until divider 332 is moved from its home position as described hereinafter.

Cartridge 314 includes an exit opening 333 which is disposed in close proximity to aerosol generator 308. Once the solution is formed within cartridge 314, it is dispensed through exit opening 333 and on to aerosol generator 308 where it will be aerosolized for delivery to the patient. Disposed across exit opening 333 is a filter 334 which serves to prevent larger drug particles from being flushed out onto aerosol generator 308, thus causing potential clogging of the apertures within aerosol generator 308.

Figure 14:
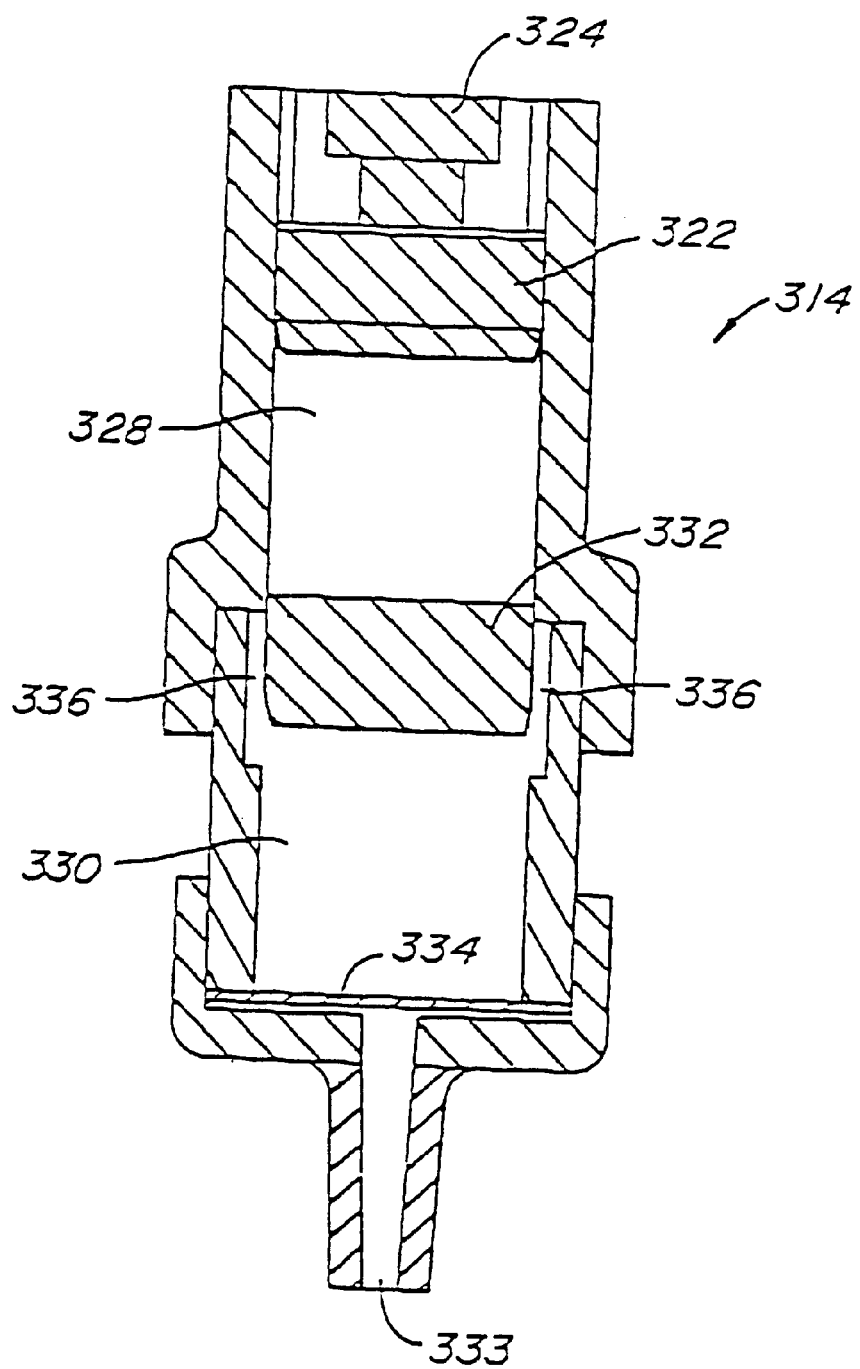
Figure 15:
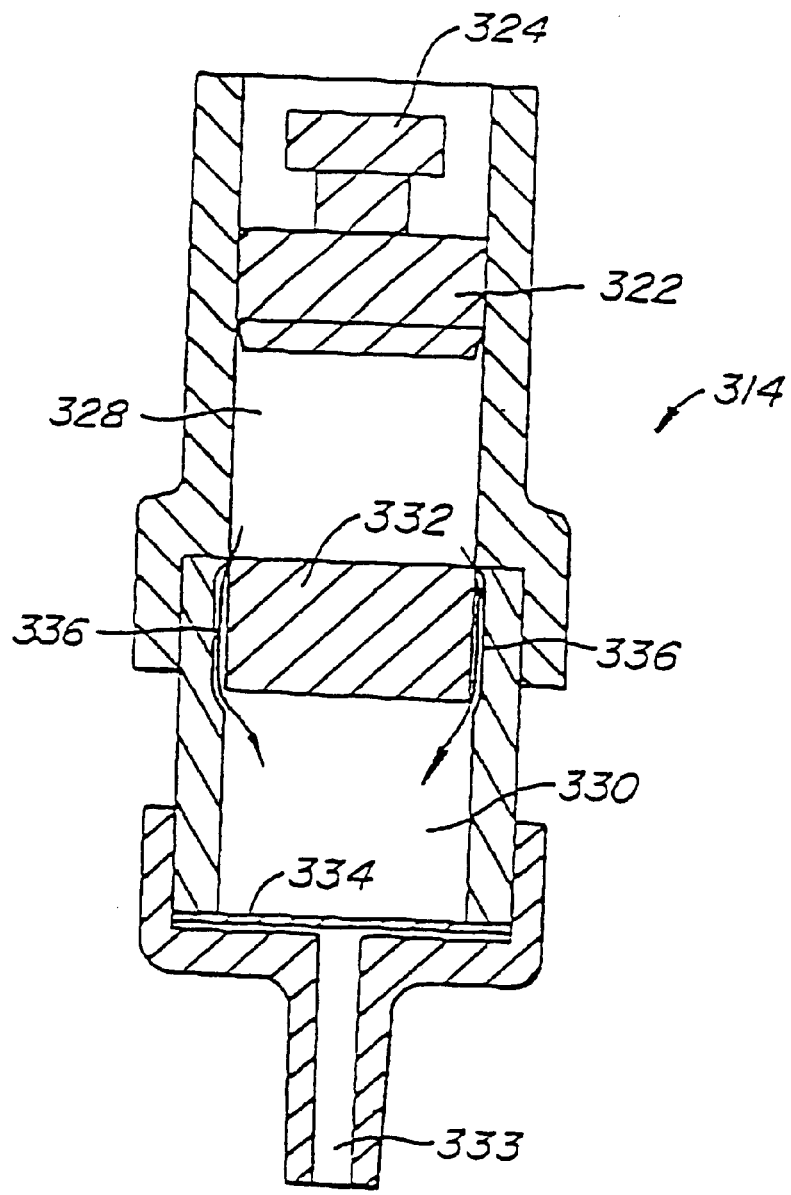

Referring now to FIGS. 14–17, operation of cartridge 314 to produce a solution which is delivered to aerosol generator 308 will be described. Cartridge 314 is constructed in a manner similar to the drug cartridge described in U.S. Pat. No. 4,226,236, the complete disclosure of which is herein incorporated by reference. As shown in FIG. 14, cartridge 314 is in the home position where divider 332 maintains the liquid within first chamber 328. When in the home position, cartridge 314 may be inserted into apparatus 300 and coupled to lead screw 316 (see FIG. 13). When ready to deliver an aerosolized solution to a patient, motor 318 (see FIG. 13) is actuated to cause lead screw 316 to translate piston 322 within cartridge 314 as illustrated in FIG. 15. As piston 322 is translated within cartridge 314, it begins to move through first chamber 328. Since the liquid is generally incompressible, the liquid will force divider 332 to move in the direction of second chamber 330. Formed in the walls of cartridge 314 are one or more grooves 336 which are placed in communication with first chamber 328 as divider 332 moves away from its home position. As such, the liquid within first chamber 328 is forced into chamber 330 as illustrated by the arrows. Once the liquid is able to flow around divider 332, the pressure acting against it is relieved so that it remains in the position generally shown in FIG. 15. As the liquid enters into second chamber 330, the lyophilized drug is dissolved into the liquid to form a solution.

Figure 16:
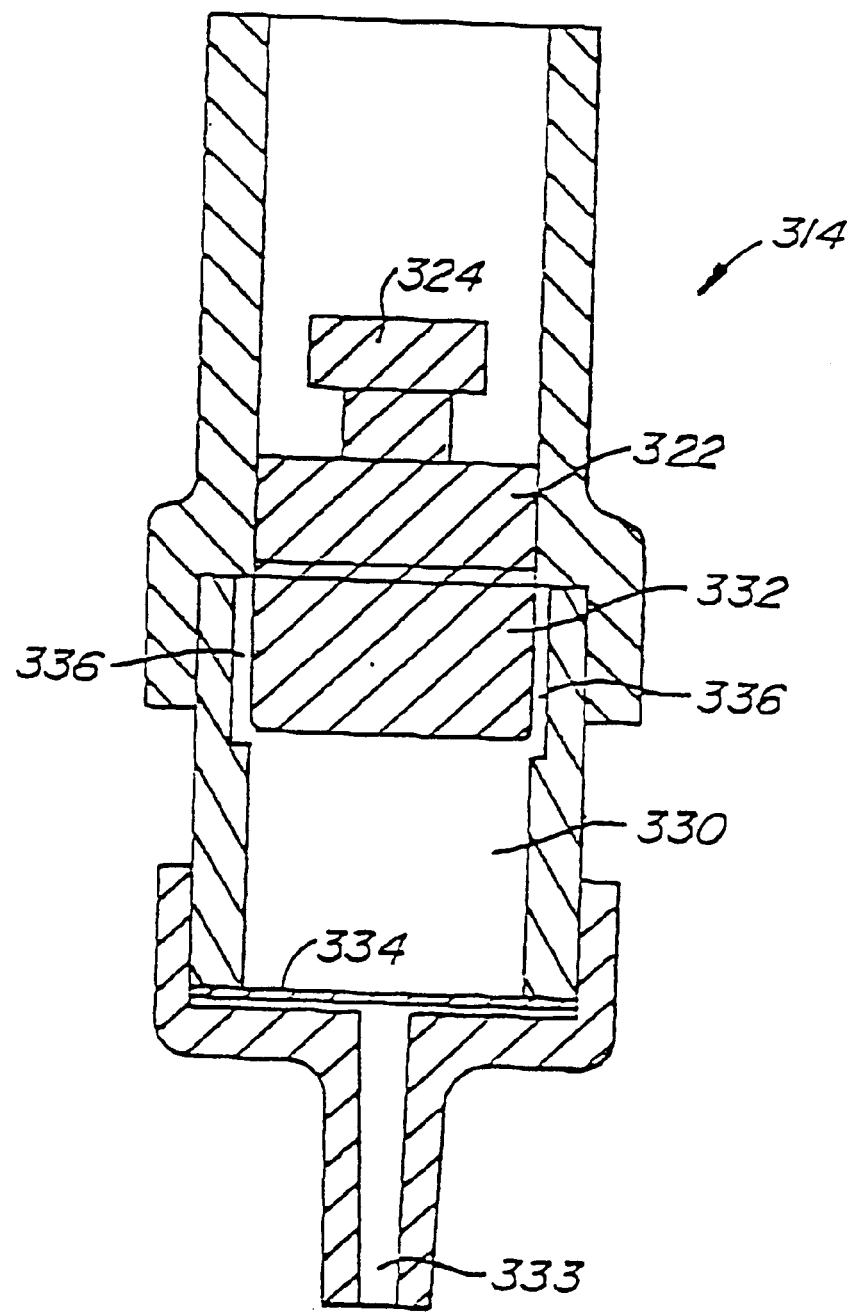

As illustrated in FIG. 16, piston 322 is translated until it engages divider 332. At this point, all of the liquid has been transferred from first chamber 328 into second chamber 330. At this point, it may optionally be desired to mix the solution that has just been formed within second chamber 330. This may be accomplished by translating piston 322 backward toward the position illustrated in FIG. 15. In so doing, a vacuum is created within first chamber 328 to draw the solution from second chamber 330 into first chamber 328. As the solution flows through grooves 336, the solution is agitated, causing mixing. Piston 322 may then be translated back to the position shown in FIG. 16 to move the liquid back into second chamber 330. This process may be repeated as many times as needed until sufficient mixing has occurred.

Figure 17:
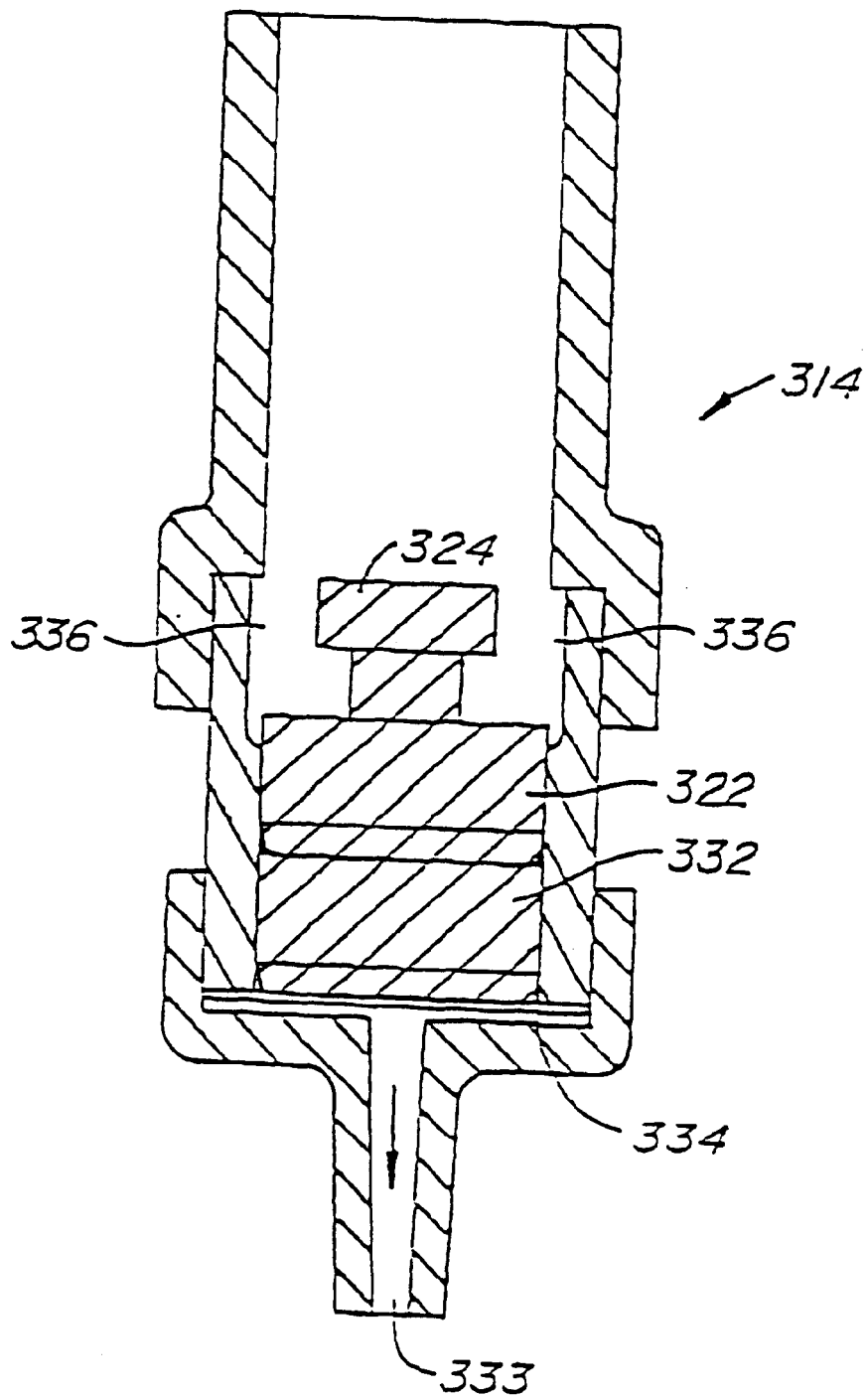
Figure 18:
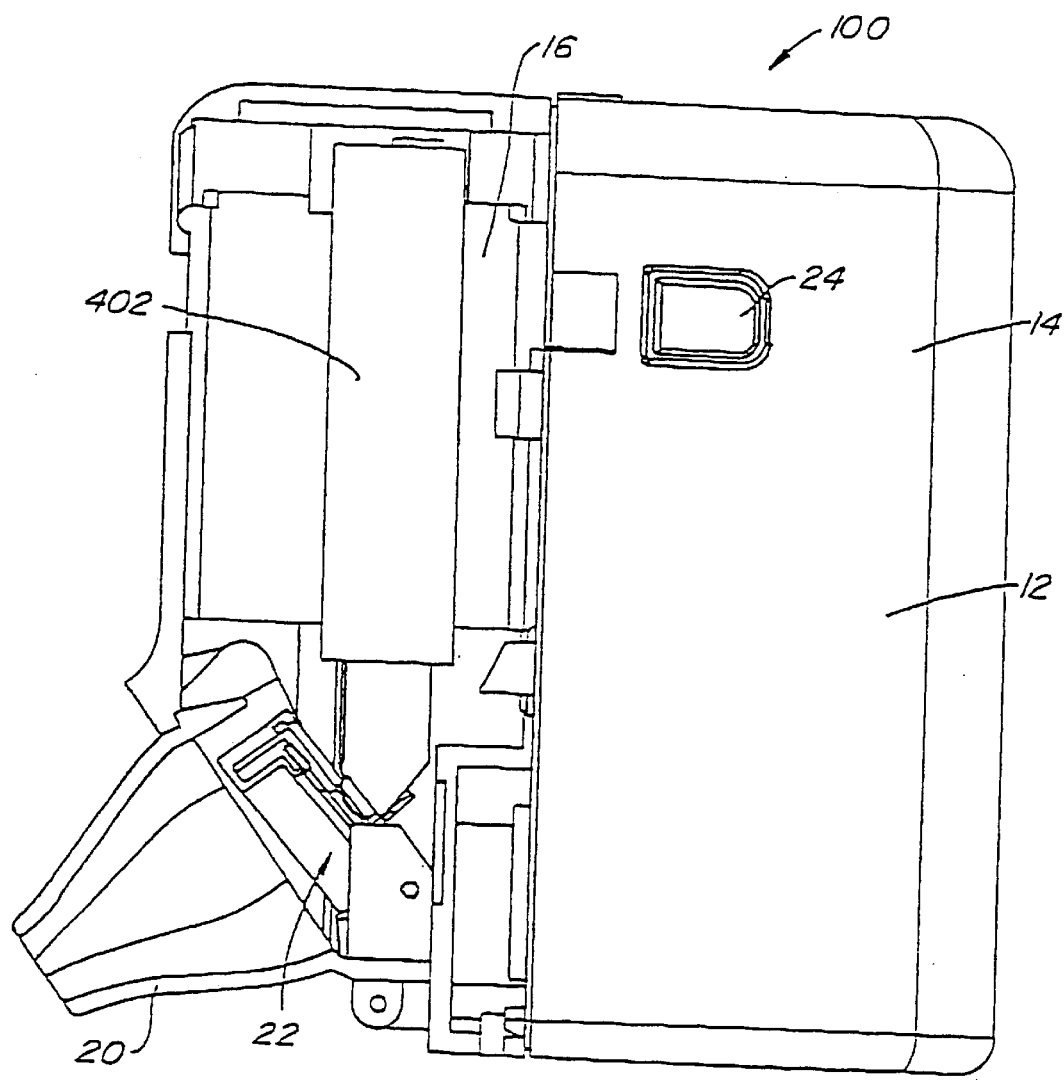
Figure 19:
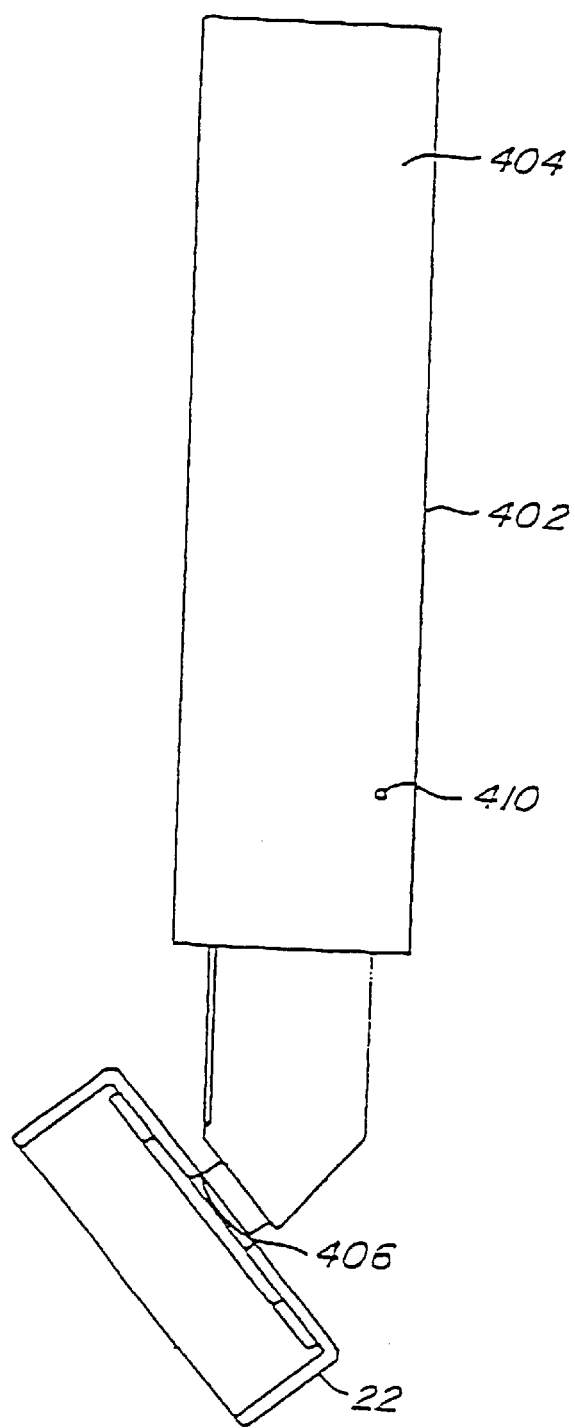
FIG. 19 illustrates the cartridge and aerosol generator of FIG. 18.
Figure 20:
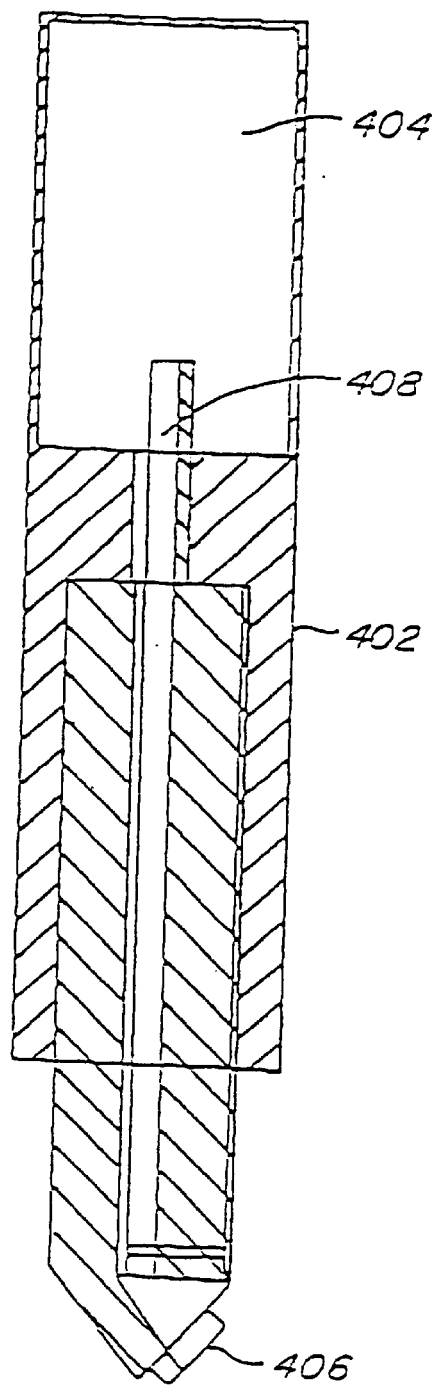
FIG. 20 is a cross-sectional view of the cartridge of FIG. 19.
Figure 21:
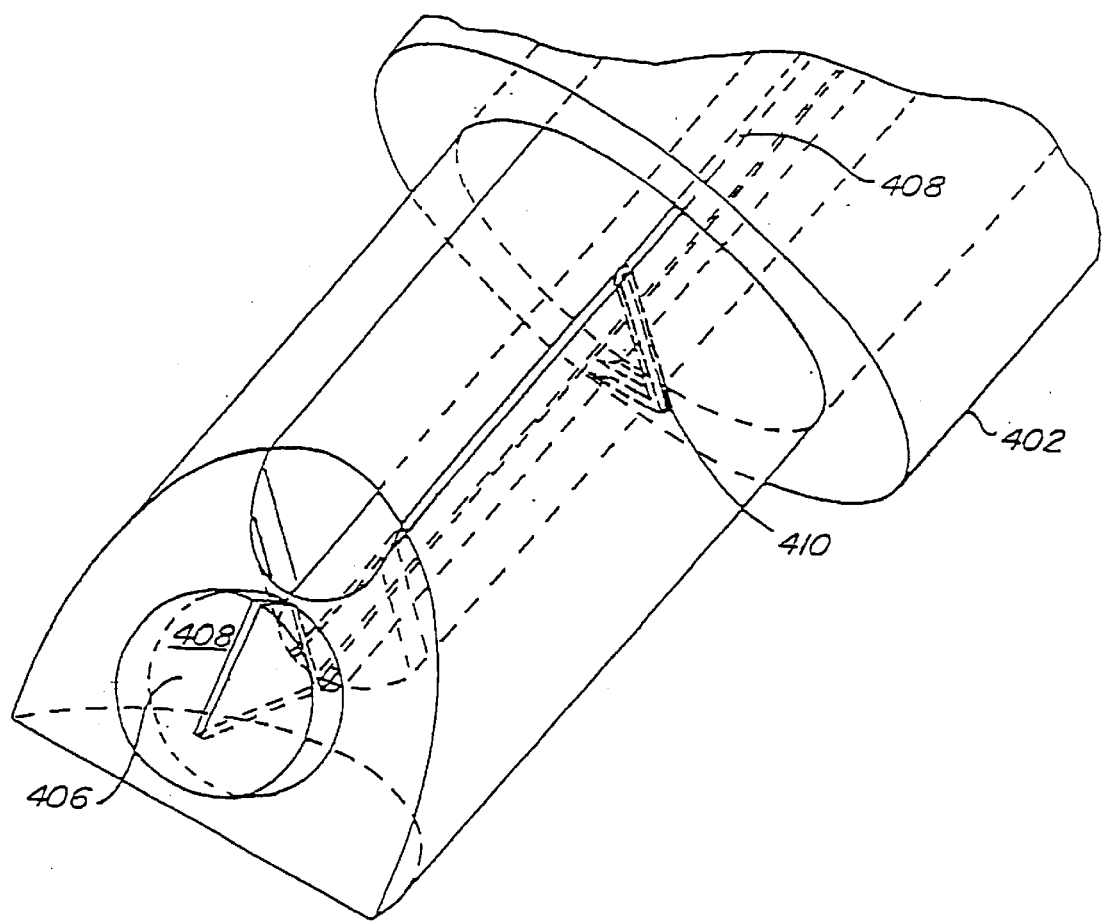
FIG. 21 is a more detailed view of the cartridge of FIG. 19.
Figure 22:
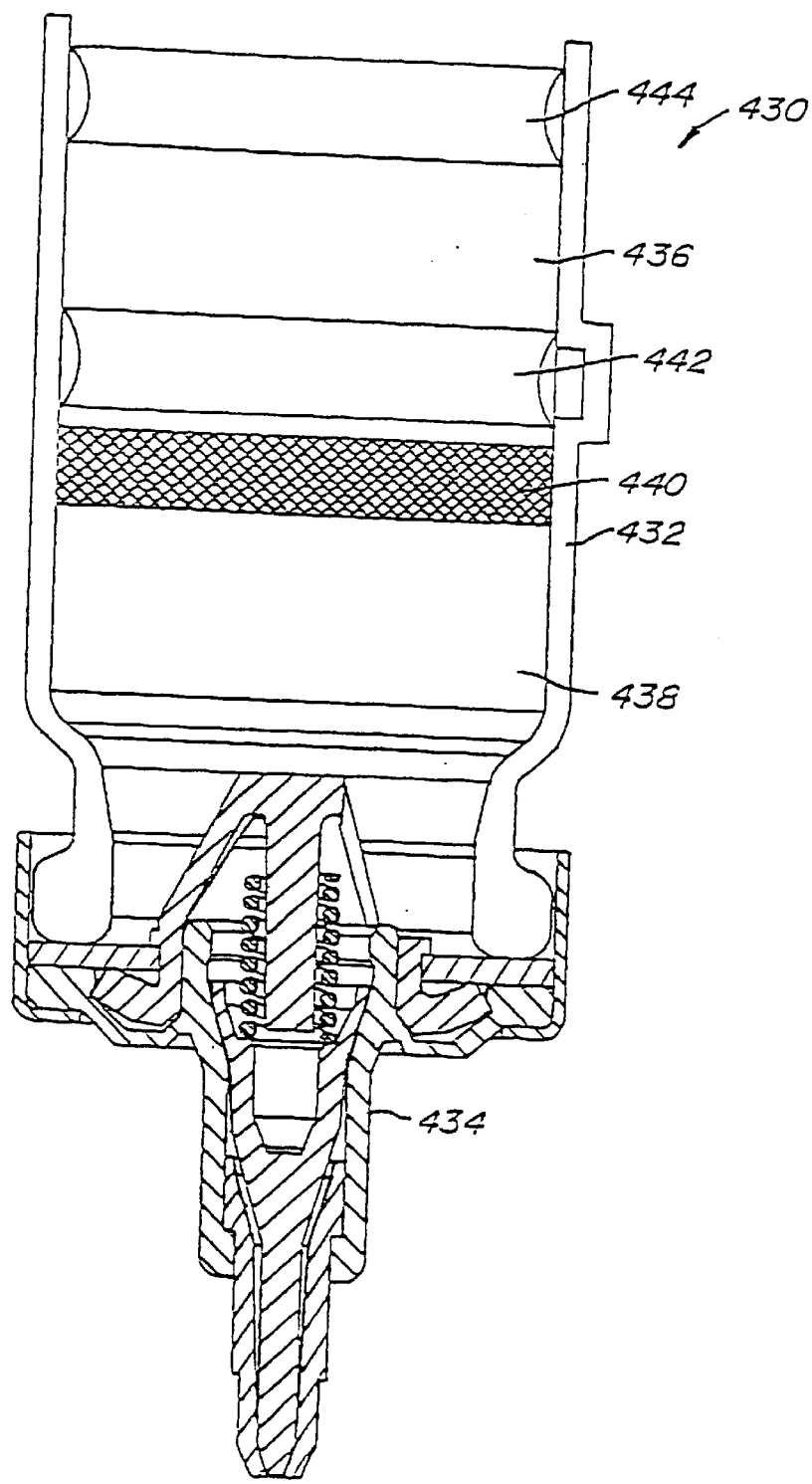
FIG. 22 is a cross-sectional side view of a dispensing system having a drug cartridge and a piston pump according to the invention.

After proper mixing, the solution is ready to be dispensed onto the aerosol generator. To do so, piston 332 is moved through second chamber 330 as illustrated in FIG. 17. In turn, divider 332 is pushed against filter 334 to completely close second chamber 330 and force all of the liquid out exit opening 333.

One particular advantage of cartridge 314 is that a precise volume of drug is dispensed onto aerosol generator 308 to ensure that the patient will receive the proper dosage. Further, by maintaining the drug in the dry state, the shelf life may be increased as previously described.

Following dispensing of the solution, cartridge 314 may be removed and replaced with another replacement drug cartridge. Optionally, a cleaning cartridge may be inserted into apparatus 300 which includes a cleaning solution. This cleaning solution is dispensed onto aerosol generator 308 upon operation of motor 318. Aerosol generator 308 may then be operated to clean its apertures using the cleaning solution.

Referring now to FIG. 18, an alternative apparatus 400 for atomizing a liquid will be described. Apparatus 400 is essentially identical to apparatus 10 except that canister 18 has been replaced with a continuous feed cartridge 402. Cartridge 402 is configured to continuously feed liquid to aerosol generator 22 on demand so that enough liquid will always be available each time aerosol generator 22 is actuated. Cartridge 402 also ensures that excessive liquid will not be supplied, i.e. it will supply only as much liquid as is atomized. Cartridge 402 is constructed similar to the cartridges described in co-pending U.S. patent application Ser. No. 08/471,311, filed Apr. 5, 1995, the complete disclosure of which is herein incorporated by reference.

As illustrated in FIGS. 19–21, cartridge 402 comprises a liquid reservoir 404 and a face 406 which is adjacent the aperture plate of aerosol generator 22 to supply liquid from liquid reservoir 404 to the aperture plate. A capillary pathway 408 extends between reservoir 404 and face 406 to supply liquid to face 406 by capillary action. In order to overcome the vacuum that is produced in reservoir 404, a venting channel 410 is in communication with pathway 408. In this way, air is able to enter into reservoir 404 to reduce the vacuum and allow additional liquid to be transferred from reservoir 404.

In another embodiment, a drug cartridge may be coupled to a piston pump to form a dispensing system that is used to supply a formation to an aerosol generator. For example, as shown in FIG. 22, a dispensing system 430 comprises a cartridge 432 and a piston pump 434. Cartridge 432 is patterned after cartridge 314 of FIG. 14 and includes a first chamber 436 and a second chamber 438. Disposed in chamber 436 is a liquid (not shown) and disposed in second chamber 438 is a dried substance 440. A divider 442 separates the chambers. In use, a plunger 444 is moved through chamber 436 to force divider 442 forward and to allow the liquid to enter chamber 438 and form a solution.

Piston pump 434 may be constructed similar to pump 138 of FIG. 4. Pump 434 is operated to dispense a volume of the solution from chamber 438. Pump 434 may be disposed near an aerosol generator so that a volume of the solution will be available for atomization. In this way, known volumes of a solution that was formed from a direct substance may be provided in an easy and convenient manner.

Referring to FIGS. 23 and 24, another aspect of the invention is shown wherein the same or similar reference numbers refer to the same or similar structure. A container 500 delivers fluid to a chamber 502. The container 500 and chamber 502 are contained within the housing 12 (FIG. 1) and the aspects of the devices described above are equally applicable here. Fluid from the container 500 fills the chamber 502 at least three times and more preferably at least twenty five times.

The chamber 502 is movable between the expanded position of FIG. 24 to the collapsed position of FIG. 23. The chamber 502 expands as fluid is delivered to the chamber 502 from the container 500 and collapses as fluid is expelled through holes 504 in a vibrating structure 506 during operation. The holes 504, which are exaggerated for clarity, are preferably shaped and sized in the manner described herein. The vibrating structure 506 is formed by the cup shaped member 44 and an element 508 having the holes 504. The element 508 has a domed shape but may be flat, curved or shaped in any other suitable manner. The vibrating structure 506 preferably vibrates at a frequency of 80–190 kHz, more preferably about 120–150 kHz, but may also operate at other frequencies. The vibrating structure 506 is vibrated with any suitable device and is preferably vibrated with the piezoelectric member 26.

The chamber 502 has a deformable wall 510 which deforms to contain varying amounts of fluid. The wall 510 preferably bows outward and away from the vibrating structure 506 when the chamber 502 expands (FIG. 24). The chamber 502 is also bounded by a back side 503 of the element 508 so that fluid in the chamber 502 is in contact with the vibrating structure 506. The chamber 502 preferably contains a volume of 10–1000 $\mu$L, more preferably 10–750 $\mu$L and most preferably about 10–500 $\mu$L when fully expanded. The wall 510 may be somewhat elastic, however, the wall 510 is preferably flexible enough that the fluid pressure in the chamber 502 is no more than 15 psi, more preferably no more than 10 psi, and most preferably no more than 5 psi when the chamber 502 is full. Fluid tension developed at the holes 504 in the vibrating structure hold the fluid within the chamber 502.

The container 500 has a piston 512 movable within a cylinder 514 containing the fluid. The piston 512 moves within the cylinder 514 to deliver a known quantity of fluid to the chamber 502. The piston 512 may be manually actuated or moved with a motor-driven actuator. The container 500 may, of course, be any other suitable device or container 500 including any other device described herein, without departing from the scope of the invention. Thus, the container 500 may have a number of compartments containing different substances and may have the valves described above.

A cap 516 is mounted to the container 500. The cap 516 has a needle 518 which pierces a septum 520 on the container 500. The cap 516 is preferably attached to the container 500 immediately before use so that the septum 520 is not pierced until just before the container 500 is mounted within the housing 12. The container 500 is then mounted to a holding element 522 with a threaded connection 524. The holding element 522 is mounted within the housing 22 in any suitable manner. The needle 518 defines a fluid path 526 between the container 500 and the chamber 502.

A valve 528 maintains sterility in the container 500 and prevents fluid flow from the chamber 502 to the container 500. The valve 528 is preferably a slit-type valve 530 but may, of course, have any other suitable structure. The valve 528 has upper and lower lips 532, 534 which connect the valve 528 to the wall 510. The valve 528 may also have a threaded connection with the wall 510 which engages the wall 510 as the container 500 engages the holding element 522.

Use of the device is now described. The cap 516 is attached to the container 500 so that the needle 518 pierces the septum 520. Alternatively, the cap 516 may be already attached to the container 500 with the valve 528 maintaining sterility of the container 500 before use. The cap 516 is then rotated into engagement with the holding element 522 which causes the valve 528 to engage and the wall 510. The user then selects a desired amount of fluid to be delivered to the chamber 502. The piston 512 is then moved an appropriate distance to deliver the desired amount of fluid. As fluid is delivered from the container 500, the valve 528 opens and the chamber 502 expands to accommodate the fluid. The chamber 502 may be completely or partially filled. As the chamber 502 is filled, the fluid pressure preferably remains within the ranges described above. The piezoelectric member 26 is then used to induce vibrations in the vibrating structure 506. Vibration of the vibrating structure 506 forces fluid from the chamber 502 through the holes 504 and out front side 507 of the vibrating structure 506.

Figure 23:
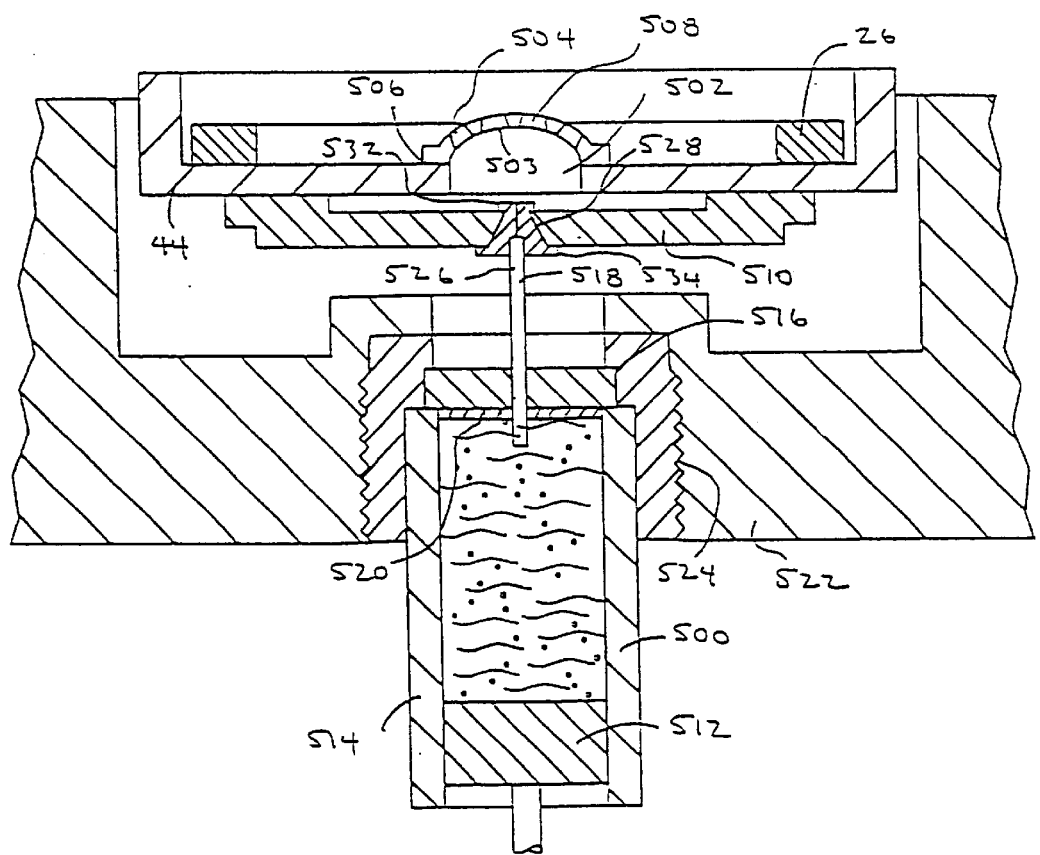
FIG. 23 shows a chamber having a deformable wall in a collapsed condition.
Figure 24:
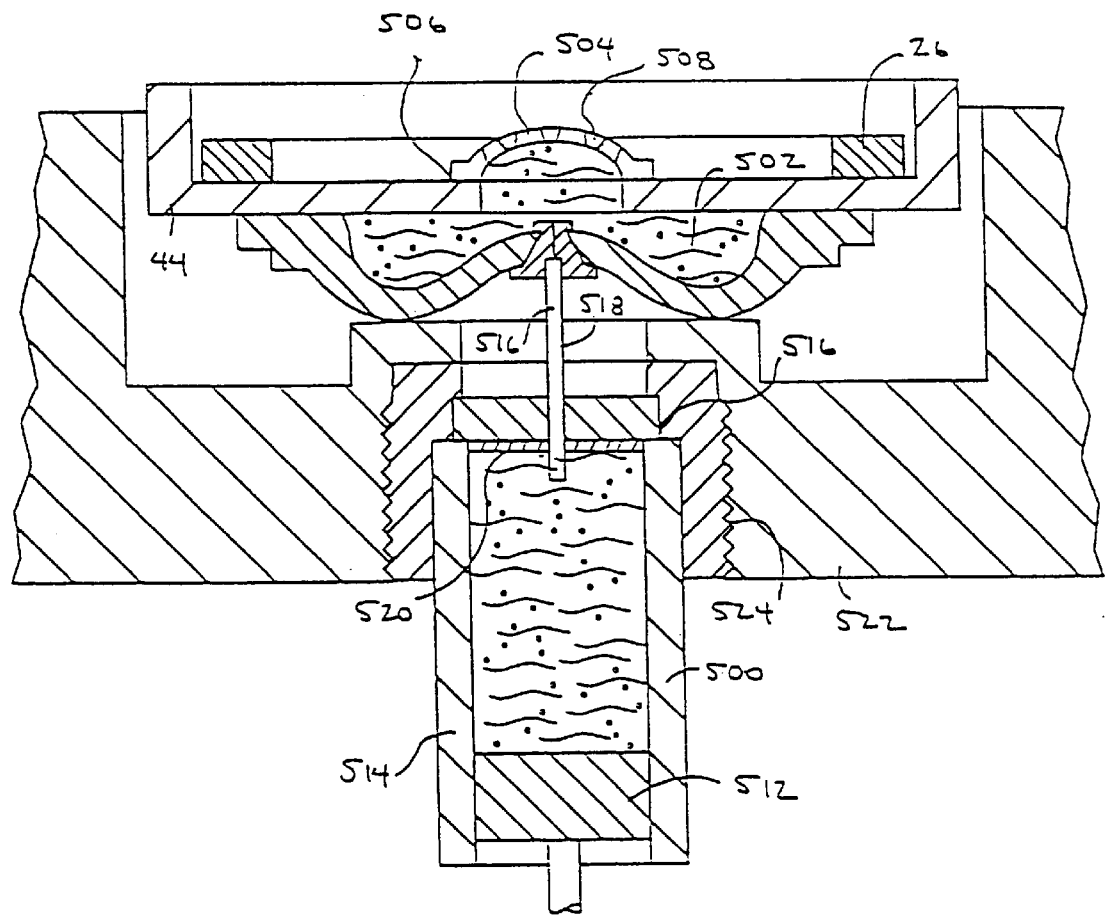
FIG. 24 shows the chamber of FIG. 23 expanded to hold fluid.
Figure 25:
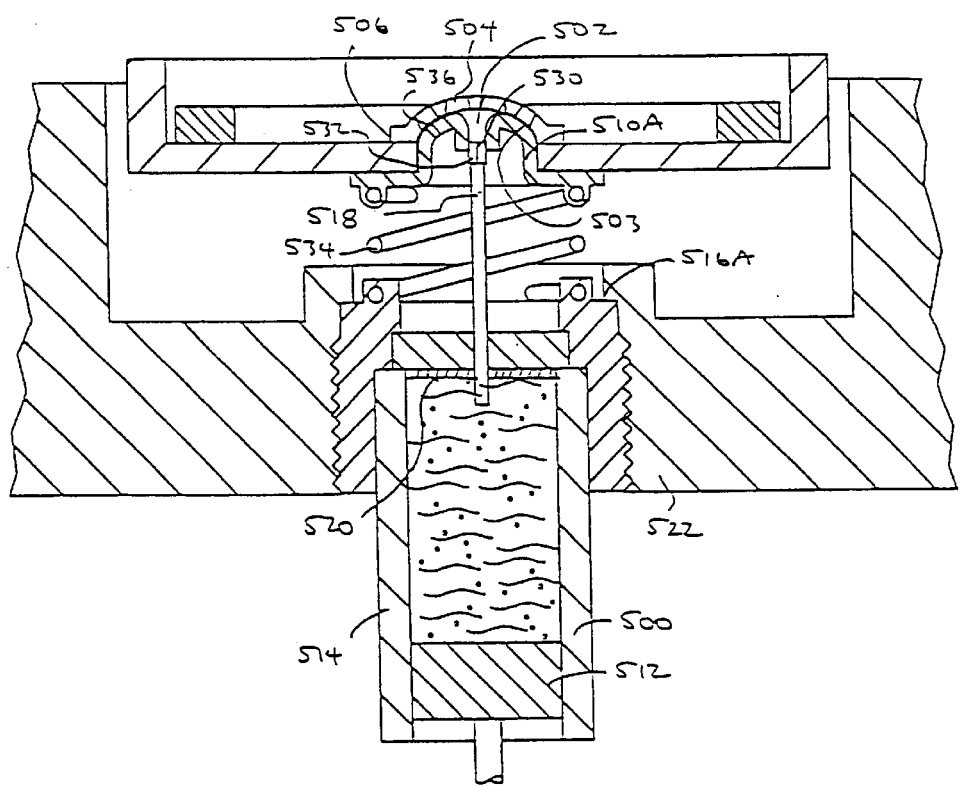
FIG. 25 shows another deformable wall for the chamber.
Figure 26:
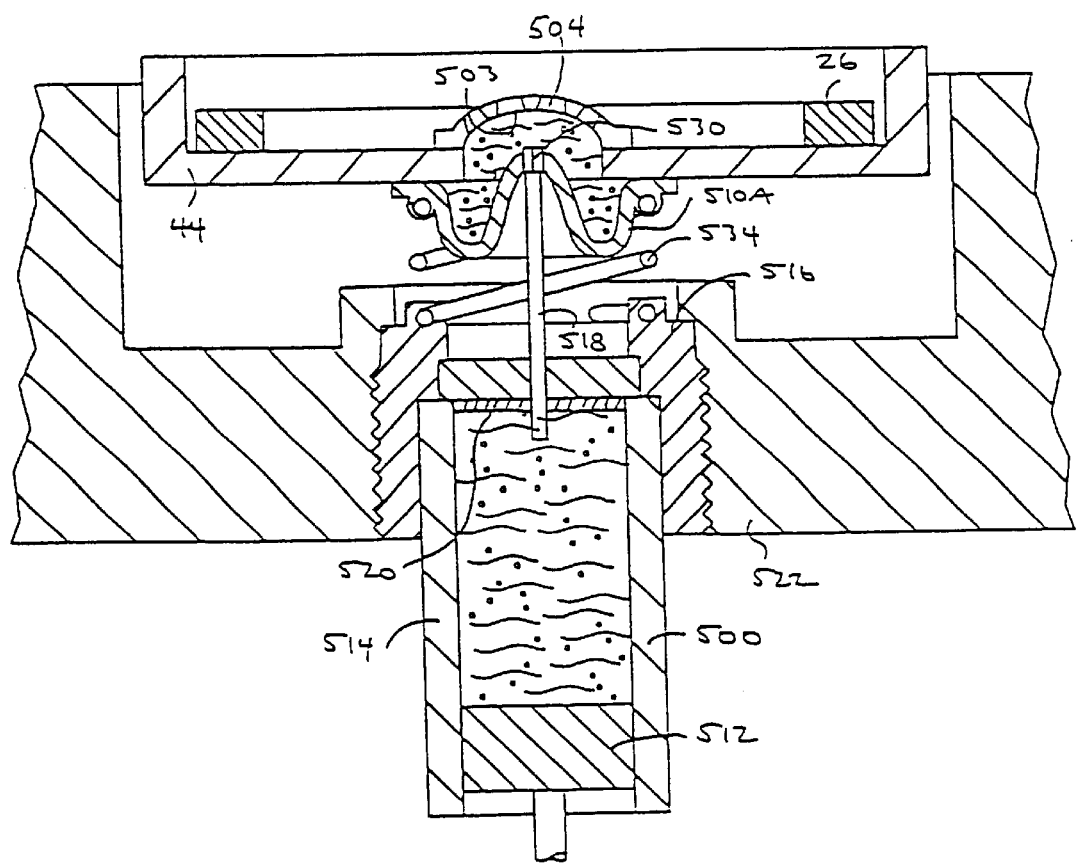
FIG. 26 shows the wall of FIG. 25 expanded to hold fluid.

Referring to FIGS. 25 and 26, another aspect of the invention is shown wherein the same or similar reference numbers refer to the same or similar structure. The dimensions, operation and use described above, such as in connection with FIGS. 23 and 24, are equally applicable here. The container 500 and chamber 502 operate similar to the container 500 and chamber 502 described above in that the container 500 delivers fluid to the chamber 502. The chamber 502 is partially defined by the back side 503 of the vibrating structure 506 and a deformable wall 510A.

The container 500 differs from the container 500 in that wall 510A may be replaced periodically and, in the preferred embodiment, is replaced with each new container 500. A cap 516A has the needle 518 for penetrating the septum 520 on the container 500 as described above. The cap 516A, needle 518, and wall 510A may be mounted to the container 500 immediately before mounting the container 500 to the holding element 522. Alternatively, the wall 510A, needle 518, cap 516A and container 500 may be packaged together. A valve 530, preferably a slit-type valve 532, is formed at the end of the needle 518 to isolate the chamber 502 from the container 500. The valve 530 defines a fluid outlet 534 positioned less than 1 mm and more preferably less than 0.5 mm from the back side 503 of the vibrating structure 506. The valve 530 is preferably positioned adjacent the holes 504 in the vibrating structure 506.

A spring 534 holds the wall 510A against the vibrating structure 506 to seal the chamber 502. The spring 534 is compressed as the container 500 is advanced into engagement with the holding element 522. The spring 534 is embedded in the wall 510A and in the cap 516A. The wall 510A is preferably made of a material that has a low bending stiffness which produces little resistance when expanding. In this manner, the pressure in the chamber may still be less than 15 psi and more preferably less than 10 psi as mentioned above. The fluid pressures are maintained at the fluid volumes mentioned above.

The wall 510A has a portion 536 which conforms to the shape of the back side 503 of the vibrating structure 522 when collapsed so that the fluid can be substantially, and preferably completely, removed from the chamber 502. In this manner, the volume remaining in the chamber 502 is less than 10 μL, more preferably less than 5 μL and most preferably less than 2 μL. The portion 536 of the wall 510A conforming to the vibrating structure 522 is preferably adjacent the holes 504 in the vibrating structure 506.

In another aspect of the invention, the vibrating structure 506 is able to drop the pressure in the chamber 502 below atmospheric pressure to help collapse the wall 510, 510A. When the vibrating structure 522 is vibrated, fluid can be forced through the holes 504 when pressure in the chamber 502 is below atmospheric pressure. The device shown in FIGS. 25–26 is used in the same manner as the device of FIGS. 23–24 and the discussion above is incorporated here.

The invention has now been described in detail, however, it will appreciated that certain changes and modifications may be made. For example, although illustrated in the context of delivering liquid to an aperture plate, the apparatus and methods may be employed to deliver known quantities of liquid to other types of atomization devices. Therefore, the scope and content of this invention are not limited by the foregoing description. Rather the scope and content are to be defined by the following claims.

What is claimed is:

1. A device for aerosolizing a liquid, comprising:

a housing;

a vibrating structure having a front side, a back side and a plurality of holes extending between the front and back sides, the vibrating structure being mounted within the housing;

means for vibrating the vibrating structure;

a chamber containing a liquid and having a deformable wall movable between a collapsed position and an expanded position, wherein the deformable wall is movable to the collapsed position to expel substantially all of the liquid from the chamber for delivery through the plurality of holes in the vibrating structure upon vibration with the vibrating means.

2. The device of claim 1, wherein:

the chamber contains a volume of less than 10 uL when in the collapsed condition.

3. The device of claim 1, wherein:

the vibrating means is a piezoelectric element coupled to the vibrating structure.

4. The device of claim 1, wherein:

the chamber contains the fluid at a fluid pressure of less than 15 psi when in the expanded position.

5. The device of claim 1, wherein:

the chamber contains the fluid at a fluid pressure of less than 5 psi when in the expanded position.

6. The device of claim 1, wherein:

the vibrating structure vibrates at a frequency of 120–150 kHz.

7. A method of aerosolizing a liquid, comprising the steps of:

providing a device for aerosolizing a liquid, the device having a housing, a vibrating structure, and a chamber, the vibrating structure having a plurality of holes therein extending between a front side and a back side, the chamber containing a liquid and being at least partially defined by a wall;

squeezing the chamber to collapse the wall, thereby delivering a desired quantity of fluid to the vibrating structure; and vibrating the vibrating structure to expel substantially all of the liquid delivered from the chamber.

8. The method of claim 7, wherein:

the delivering step is carried out with a fluid pressure of less than 15 psi in the chamber.

9. The method of claim 7, further comprising the step of:

removing and replacing the wall.

10. The method of claim 7, wherein:

the providing step is carried out with the wall having a portion which generally conforms to a shape of the back side of the vibrating structure when in the collapsed position.

11. The method of claim 7, wherein:

the providing step is carried out with the wall mounted to the vibrating structure.

12. The method of claim 7, wherein:

the vibrating step is carried out with the pressure in the chamber being less than a pressure at the front side of the vibrating structure.

* * * * *